United States Patent
Unosson et al.

(10) Patent No.: US 12,383,474 B2
(45) Date of Patent: Aug. 12, 2025

(54) STABILIZED AMORPHOUS CALCIUM MAGNESIUM PHOSPHATE PARTICLE COMPOSITIONS

(71) Applicant: PSILOX AB, Uppsala (SE)

(72) Inventors: Erik Unosson, Uppsala (SE); Tomas Lindström, Uppsala (SE)

(73) Assignee: PSILOX AB, Uppsala (SE)

( * ) Notice: Subject to any disclaimer, the term of this patent is extended or adjusted under 35 U.S.C. 154(b) by 643 days.

(21) Appl. No.: 17/771,856

(22) PCT Filed: Oct. 23, 2020

(86) PCT No.: PCT/SE2020/051029
§ 371 (c)(1),
(2) Date: Apr. 26, 2022

(87) PCT Pub. No.: WO2021/086252
PCT Pub. Date: May 6, 2021

(65) Prior Publication Data
US 2022/0296477 A1    Sep. 22, 2022

(30) Foreign Application Priority Data

Oct. 30, 2019   (SE) .................................... 1951240-9

(51) Int. Cl.
| | | |
|---|---|---|
| A61K 8/02 | (2006.01) | |
| A61K 8/04 | (2006.01) | |
| A61K 8/24 | (2006.01) | |
| A61K 8/34 | (2006.01) | |
| A61K 8/42 | (2006.01) | |
| A61Q 11/00 | (2006.01) | |
| C01B 25/45 | (2006.01) | |

(52) U.S. Cl.
CPC ............ *A61K 8/025* (2013.01); *A61K 8/0279* (2013.01); *A61K 8/042* (2013.01); *A61K 8/24* (2013.01); *A61K 8/345* (2013.01); *A61K 8/42* (2013.01); *A61Q 11/00* (2013.01); *C01B 25/45* (2013.01); *A61K 2800/412* (2013.01); *A61K 2800/621* (2013.01); *C01P 2002/02* (2013.01); *C01P 2002/72* (2013.01); *C01P 2004/03* (2013.01); *C01P 2004/34* (2013.01); *C01P 2004/62* (2013.01); *C01P 2006/12* (2013.01)

(58) Field of Classification Search
CPC ...... A61K 8/025; A61K 8/0279; A61K 8/042; A61K 8/24; A61K 8/345; A61K 8/42; A61K 2800/412; A61K 2800/621; A61Q 11/00; C01B 25/45; C01P 2002/02; C01P 2002/72; C01P 2004/03; C01P 2004/34; C01P 2004/62; C01P 2006/12
See application file for complete search history.

(56) References Cited

U.S. PATENT DOCUMENTS

2016/0235683 A1    8/2016    Powell et al.

FOREIGN PATENT DOCUMENTS

| CN | 107619031 A | | 1/2018 | | |
|---|---|---|---|---|---|
| WO | WO-2011016772 A1 | * | 2/2011 | ........... | A61K 6/0017 |
| WO | WO-2014148997 A1 | * | 9/2014 | ........... | A61K 6/0008 |
| WO | WO-2017082811 A1 | * | 5/2017 | | |

OTHER PUBLICATIONS

"Amorphous calcium phosphate and its application in dentistry", Chem Cent J. 2011; 5:40. Published online Jul. 8, 2011. doi: 10.1186/1752-153X-5-40.

"Fluoride-doped amorphous calcium phosphate nanoparticles as a promising biomimetic material for dental remineralization", Michele Iafisco et al., Scientific Reports vol. 8, Article No. 17016 (2018), Nov. 19, 2018, https://doi.org/10.1038/s41598-018-35258-x.

Indian Examination Report regarding Patent Application No. 202217030020, dated Jan. 12, 2024.

Qin, T. et al."A novel method to synthesize low-cost phosphate-based particles from natural water", Materials Letters 206 (2017) 178-181.

Qin, T. et al., "A novel rapid synthesis, characterization and applications of calcium phosphate nanospheres from Baltic seawater", Ceramics International 44 (2018) 9076-9079.

Qi, C. et al., "Porous microspheres of magnesium whitlockite and amorphous calcium magnesium phosphate: microwave-assisted rapid synthesis using creatine phosphate, and application in drug delivery", Journal of Materials Chemistry B, 2015, 3, 7775-7786.

* cited by examiner

*Primary Examiner* — Robert A Wax
*Assistant Examiner* — John W Lippert, III
(74) *Attorney, Agent, or Firm* — Harness, Dickey & Pierce, P.L.C.

(57) ABSTRACT

The present invention relates to a particle composition comprising XRD amorphous calcium magnesium phosphate particles and a method for manufacturing such a composition. The XRD amorphous calcium magnesium phosphate particles are spherical particles with a hollow core. The particle-containing paste may be used in dental products such as toothpaste to treat dentin hypersensitivity by mineralizing and occluding exposed dentin tubules.

41 Claims, 10 Drawing Sheets

STABILIZED AMORPHOUS CALCIUM MAGNESIUM PHOSPHATE PARTICLE COMPOSITIONS

CROSS-REFERENCE TO RELATED APPLICATIONS

This application is a 371 U.S. National Phase of International Application No. PCT/SE2020/051029, filed on Oct. 23, 2020, which claims priority to Sweden Patent Application No. 19512409, filed on Oct. 30, 2019. The entire disclosures of the above applications are incorporated herein by reference.

FIELD OF THE INVENTION

The present invention relates to spherical and hollow calcium magnesium phosphate particles, and compositions comprising said particles and methods for preparing the particles and the compositions. The particles and compositions comprising said particles may be used in e.g. toothpaste and for treating hypersensitive teeth by increasing the mineralization in particular deep into the dentin tubules.

BACKGROUND

Dentin hypersensitivity is a widespread and clinically relevant problem, which is characterized as a sharp and sudden pain occurring as a response to external thermal, mechanical, osmotic or evaporative stimuli. Hypersensitivity can occur if there is a loss of protective cover of the dentin due to loss of enamel or if the cementum is exposed due to gingival recession, thereby opening up the dentin tubules to the oral environment. Loss of enamel can be a result of abrasion, erosion or abfraction. Gingival recession becomes more frequent with age but can also occur in younger individuals due to e.g. aggressive tooth brushing, pocket reduction surgery, excessive flossing or as a secondary reaction to periodontal diseases.

Amorphous calcium phosphate (ACP) is a metastable phase that lacks long range crystalline order and is thus more soluble than crystalline calcium phosphates such as hydroxyapatite (HA) and tricalcium phosphate (TCP). The higher solubility of ACP makes it more bioactive as bioavailable calcium and phosphate ions are more readily released to the local environment. It has been demonstrated that ACP acts as a precursor to apatite in teeth, and thus constitutes an important part in natural mineralization. This has made development of synthetic ACP for biomedical applications an intriguing research field, but few successful processes have been reported due to its inherent metastability and subsequent limitations in handling and product formulations. As a consequence, many commercially available products rely on in situ precipitated ACP, for example by providing the calcium salts and phosphate salts through a dual-barrel type of delivery just before being applied on the tooth surface.

To make use of synthetic ACP in biomedical applications it needs to be stabilized or formulated in such a way that it does not prematurely crystallize and thereby loose part of its bioactive properties. Stabilization of ACP can be achieved for example by Mg substitution or by use of milk derived casein phosphopeptide (CPP).

WO2014/148997A1 (WO'997) discloses crystalline calcium phosphate particles that are essentially free from strontium for the use in the treatment of exposed dentin tubules. However, these particles are less soluble and therefore will not as readily act as a source for calcium and phosphate ions.

CN107619031A discloses methods for preparing calcium phosphate and magnesium phosphate spherical particles, including the use of lake or sea water as a source of calcium and magnesium ions.

There is a need for ACP particles that remain stable in their amorphous state during storage, and a composition comprising the ACP particles in which the particles are stable. Another need in the area is stabilized ACP particles with controlled morphology and free from potential allergens, which also can be produced at a large scale.

SUMMARY OF THE INVENTION

The present invention aims at solving the problems of the prior art by providing a composition for stabilizing ACP particles as well as a scalable and controlled continuous manufacturing process of forming such particles and compositions. Stabilizing the particles directly in the manufacturing process with a paste forming compound increases stability and shelf-life of the particles and facilitates formulation of particle-containing product formulations. It also reduces the risk of particle aggregation, which otherwise can cause particle formulation inhomogeneity and also reduce the particles ability to penetrate into the dentin tubules. Also, by forming the composition directly rather than drying, milling and sieving to form a fine powder, any safety concerns related to airborne particles from product handling is minimized.

The average diameter of dentin tubules is approximately 2 μm, and the present invention provides particles of appropriate size that more easily penetrate the dentin tubules, exhibit suitable affinity with dentin and which allow a higher release of ions as a result of the amorphous state of the particles. This promotes a more efficient treatment of exposed dentin tubules by increasing the mineralization thereof. Furthermore, using the particles according to the present invention for mineralizing the dentin tubules provides surfaces that are more resistant to wear and acid etching. By forming a particle-containing product formulation, e.g. a toothpaste, a desensitizing gel, a varnish or a sealant, the present invention may easily be applied to the treatment site. The method according to the present invention for preparing the particles makes it easy to prepare the particles and the composition in a controlled manner with repeatable results at different manufacturing output scales and the method may be performed in a continuous manner.

In a first aspect the invention relates to a composition comprising a paste forming compound and XRD amorphous calcium magnesium phosphate spherical particles having a hollow core and a shell wherein the particles are XRD amorphous and wherein the shell of the particles comprises 15-30 weight % of calcium, 50-70 weight % of phosphate, 5-11 weight % magnesium, and 1 to 20 weight % bound water, and wherein the Ca/P molar ratio is in the range of 0.70 to 1.20, and wherein the (Ca+Mg)/P molar ratio is in the range of 1.00 to 1.70, and wherein the particles have a mean particle size in the range of 100 to 500 nm, and wherein the amount of particles in the composition is 25-50 weight %.

In a second aspect the invention relates to a method of preparing a composition comprising the steps of:
 a. providing a first aqueous solution having a pH of 6 to 10 and a first temperature, wherein said first solution comprises dihydrogen phosphate and/or hydrogen phosphate ions and one or more counter ions preferably selected from sodium and/or potassium;

b. providing a second aqueous solution having a second temperature, wherein said second solution comprises calcium and magnesium ions and one or more counter ions preferably selected from chloride, sodium and/or potassium; and wherein the amount of calcium is in molar excess of magnesium;

c. heating the first aqueous solution, the second aqueous solution or both the first and the second aqueous solutions to a first and second elevated temperature respectively;

d. bringing the first and second aqueous solutions into contact with each other giving a third aqueous solution having a third temperature and wherein the amount of phosphate in the third aqueous solution is in molar excess to the total amount of calcium and magnesium;

e. allowing particles to form;

f. collecting the formed particles;

g. optionally washing the isolated particles using a suitable solvent;

h optionally dewatering the washed particles at a fifth temperature until a slurry comprising 70-95 weight % free water is obtained, preferably 75-85 weight %;

i. mixing the spherical particles with a paste forming compound wherein the amount of particles in the composition is 25-50 weight %;

j. dewatering of the mixture of spherical particles and paste forming compound at a seventh temperature; and k. optionally homogenizing the mixture of spherical particles and paste forming compound of to obtain a composition.

In a third aspect the invention relates to the use of the composition according to the present invention as an ingredient in a toothpaste, a desensitizing gel, a bleaching paste, a dental varnish, a dental prophy paste, a pit and fissure sealant, a dental filling material, a capping material, a mouth wash, an interdental cleaning instrument, a chewing gum, an implant, a bone graft material, a bone void filling material.

In a fourth aspect the invention relates to a toothpaste, a desensitizing gel, a bleaching paste, a sealant, a dental varnish or a dental prophy paste comprising the composition according to the present invention wherein the amount of particles is 0.5 to 15 weight %.

In a fifth aspect the invention relates to a bleaching paste comprising the composition according to the present invention and carbamide peroxide, wherein the amount of particles is 3-10 weight % and the amount of carbamide peroxide is 10-20 weight %.

All embodiments disclosed herein relates to all aspects of the present invention and all embodiments may be combined unless stated otherwise.

DETAILED DESCRIPTION OF THE INVENTION

Figure 1:
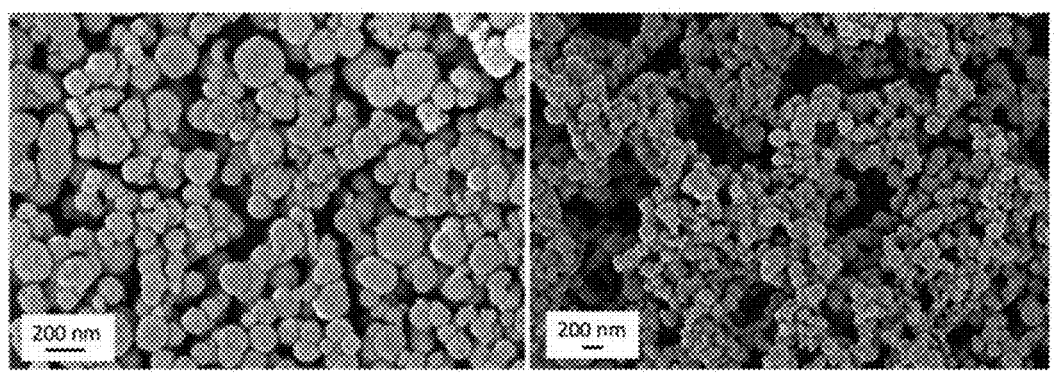
FIG. 1. SEM images of calcium magnesium phosphate particles.

In the present application the term "mean particle size" corresponds to the mean particle size of individual particles and fused particles forming small clusters. Mean particle size is determined using dynamic light scattering (DLS).

In the present application the term 'stable' refers to stable in terms of chemical composition, and/or particle morphology, and/or crystallinity, and/or mean particle size, and/or particle surface area, and/or physical properties such as viscosity with regards to compositions. Hence, a stable particle or stable composition may mean that a composition, or particles, remain essentially the same during storage for an extended period of time, such as 12 months or considerably longer.

In the present application the term "X-ray diffraction (XRD) amorphous" refers to a material or particles that lacks long range crystalline order. The crystallinity or XRD amorphous state of the particles is determined by powder X-ray diffraction using Cu-Ka ($\lambda$=1.5406 Å), scanning $2\theta$ from 7 to 60° with a step size of approximately 0.02°. A crystalline material reflects the X-rays according to the arrangement of its crystallographic planes and generates an identifiable pattern of sharp peaks, whereas an XRD amorphous material only generates a single broad diffuse peak. In the present application the particles are thus classified as XRD amorphous if the generated pattern lacks identifiable sharp peaks and is only characterized by a broad diffuse peak.

In the present application the term "bound water" corresponds to water of hydration associated to the amorphous calcium magnesium phosphate particles. This bound water is part of the particle chemical formula, i.e. the particles have the chemical formula $Ca_wMg_xH_y(PO_4)_z \cdot nH_2O$. The term "free water" denotes any residual or excess water that is not part of the particle chemical formula. Free water may for example be part of the composition according to the present invention, or water used in the process of forming the ACP particles and/or the composition.

The object of the present invention is to provide particles, compositions and a particle-containing product formulation which facilitate fast and efficient mineralization of dentin tubules. The purpose of the particles is not only to mechanically block or fill the void of the dentin tubules but also to mineralize said tubules. Without being bound by theory it is therefore believed that the particles need to be in an amorphous state when delivered to the treatment site in order to rapidly and efficiently release calcium and phosphate ions to create local supersaturation and subsequent precipitation of hydroxyapatite-like mineral. Hence the object encompasses providing stable particles, in particular with regard to crystallinity, during storage. The present inventors have shown (Example 20) that the present invention results in much faster occlusion of dentin tubules in comparison with more crystalline calcium phosphate particles according to WO2014/148997A1.

Figure 2:
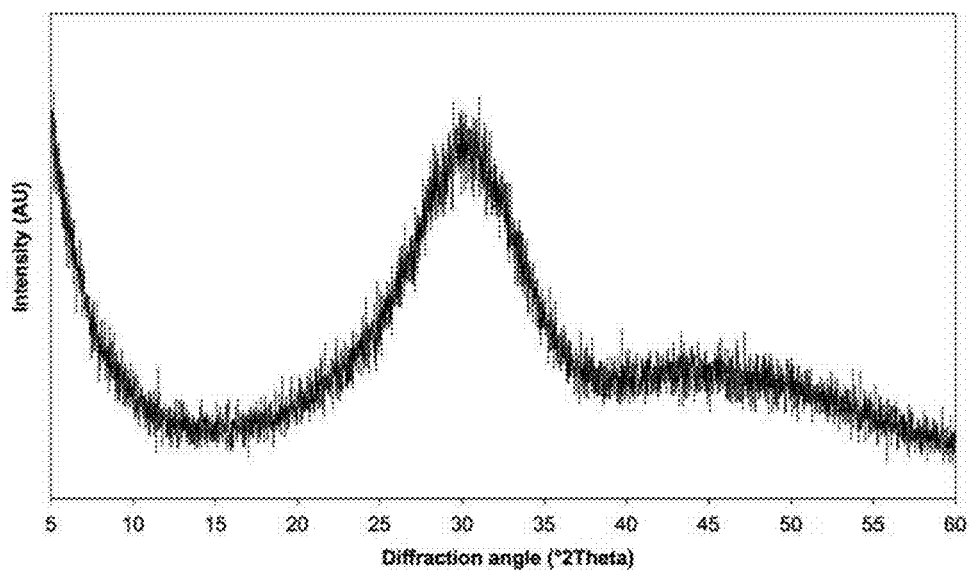
FIG. 2. XRD pattern of calcium magnesium phosphate particles. The particles are XRD amorphous.

The particles of the present invention are spherical particles having a hollow core and a shell, see FIG. 1. The shell is preferably porous in order to facilitate a faster release of ions from the particles itself or release of substances loaded inside the particle's hollow core. The pores are preferably around 1-30 nm in diameter. Since the particles are XRD amorphous, see FIG. 2, they more easily dissolve and release ions which then participate in the remineralization of the dentin tubules. In a preferred embodiment the particles have a crystallinity that is essentially long range amorphous but can be short range (nano) crystalline if resolved with e.g. a high resolution transmission electron microscope (HR-TEM). Without being bound by theory spherical particles having a mean particle size in the range of 100-500 nm are believed to more easily penetrate deep into the dental tubules than for example larger spherical particles or particles in the shape of rods or flakes. It is further believed that the X-ray amorphous character of the particles is a result of the magnesium substitution, the bound water and the method of forming the present particles.

Calcium, phosphate and magnesium are the main components of the particles or the shell of the particles and the shell of the particles comprises 15-30 weight % of calcium, 50-70 weight % of phosphate, 5-11 weight % magnesium, and 1 to 20 weight % bound water, and wherein the Ca/P molar ratio is in the range of 0.70 to 1.20, and wherein the (Ca+Mg)/P molar ratio is in the range of 1.00 to 1.70. The magnesium substitutes the calcium in the calcium phosphate crystal structure. In order for the particles to form a nice composition or formulation and in order for the particles to penetrate the dentin tubules, which are approximately 2 µm in diameter, the particles have a mean particle size in the range of 100 to 500 nm.

Figure 3:
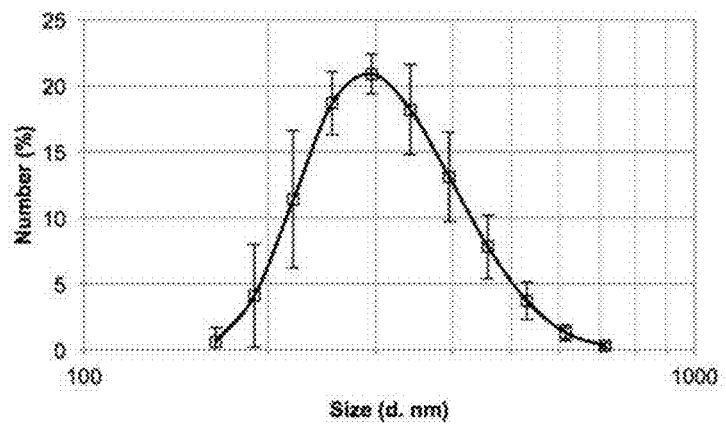
FIG. 3. DLS particle size distribution of the calcium magnesium phosphate particles.

It is preferred that the particles are not so small that they exhibit a too positive buoyancy and dissolve too fast, or too big so they cannot penetrate deep into the dentin tubules, and that they have a narrow size distribution, see FIG. 3. An advantage of the present invention is that the particles of the composition are not agglomerated into larger clusters. In one preferred embodiment the mean particle size is 150-450 nm, more preferably 250-350 nm. The content, or composition, of the particles or the shell of the particles may vary. For example, the amount of bound water, or degree of hydration, depends on the drying process when preparing the particles or the composition. In a preferred embodiment the amount of bound water is 12-16 weight %. It is believed that by having bound water in the particles the ability of the particles to crystallize is suppressed and instead the particles remain amorphous.

Preferably the calcium content in the particles is 18 weight % or higher, or 20 weight % or higher but preferably 25 weight % or lower, or more preferably 23 weight % or lower, more preferably 22 weight % or lower. Preferably the phosphate ($PO_4$) content in the particles is 55 weight % or higher, or more preferably 58 weight % or higher but preferably 65 weight % or lower, more preferably 62 weight % or lower. Preferably the magnesium content in the particles is 6 weight % or higher, or preferably 7 weight % or higher but preferably 9 weight % or lower, more preferably 8 weight % or lower. For the particles to be XRD amorphous the degree of magnesium substitution of calcium should be sufficiently high and preferably at least 20 mol %, more preferably 25-50 mol %, more preferably 30-35 mol %.

Since the remineralization process is partly dependent on the presence of ions such as calcium, magnesium and phosphate the ratio of these ions in the particles is important. Preferably the Ca/P molar ratio is 0.8 or higher, more preferably 0.9 or higher, preferably 1.1 or lower, more preferably 1.0 or lower. Preferably the (Ca+Mg)/P molar ratio is 1.2 or higher, more preferably 1.3 or higher, preferably 1.5 or lower, more preferably 1.4 or lower.

In one preferred embodiment the content of the shell of the particles comprises 21-24 weight % of calcium preferably 22-23 weight %, 56-60 weight % of phosphate preferably 58-59 weight %, 5-8 weight % magnesium preferably 6-7 weight % and 12-16 weight % of bound water preferably 13-15 weight %. The Ca/P ratio is 0.8-1.1 preferably 0.9-1.0 and the (Ca+Mg)/P ratio is 1.2-1.5 preferably 1.3-1.4.

In another preferred embodiment the content of the shell of the particles comprises 20-26 weight % of calcium, 52-64 weight % of phosphate, 5-9 weight % of magnesium and 12-16 weight % bound water and wherein the Ca/P ratio is 0.80-1.00 and the (Ca+Mg)/P ratio is 1.15-1.45.

The particles of the present invention may further contain other ions such as sodium, potassium, silicon, zinc and fluoride. Preferably the content of said ions is 0.1 to 3 weight %, preferably less than 2 weight %, more preferably less than 1 weight %. In one embodiment the particles comprise one or more of sodium, potassium and fluoride. The particles are preferably free from or essentially free from strontium.

Average surface area determined by the Brunauer-Emmett-Teller (BET) method using nitrogen gas is preferably 10-40 $m^2/g$, more preferably 15-35 $m^2/g$, more preferably 20-30 $m^2/g$. A higher surface area results in that the particles dissolve faster but the particles should not dissolve before application and before entering the dentin tubules.

The present inventors have shown that the particles of the present invention results in an increase in pH upon dissolution in aqueous media which facilitate nucleation and growth of hydroxyapatite mineral on the dentin surface and inside exposed dentin tubules, see Example 18. This is advantageous since during use the particles will dissolve in saliva or dentin liquor and hence, likely facilitate nucleation and growth of hydroxyapatite mineral.

In order for the particles to be remineralization efficient they have to be stable, particularly in their XRD amorphous state. It is preferred that the particles remain XRD amorphous during storage for at least 24 months, i.e. that they have a shelf life of at least 24 months. In this way it is possible to manufacture the particles at one site and deliver them for product formulation at another site without deteriorating the remineralization property. Another advantage with particles that remain XRD amorphous is that they can be stored on the shelf for a time-period prior to use, and hence do not need to be used directly upon manufacturing.

It is believed that the particles remain in their XRD amorphous state if the amount of free water is reduced. This can for example be achieved by formulating the particles together with a paste-forming compound that is essentially free of water, such as <10 weight %, in order to form a composition. The present invention provides a process of forming such a composition with homogeneously dispersed particles, limited amount of free water, and stable properties. Such a process of forming said composition may also be advantageous in terms of preparation of an end product such as for example a toothpaste to which the composition may be added. Hence, it is an advantage that the composition has good flowability and/or viscosity and can easily be mixed with other ingredients to prepare for example a toothpaste.

The particles of the present invention are preferably used or formulated in a composition which preferably is in the form of a slurry or suspension. The composition comprises, besides the particles a paste forming compound preferably selected from glycerol, triglyceride, polyethylene glycol, propylene glycol, polypropylene glycol, polyvinyl alcohol, mineral oil or liquid paraffin or a combination thereof. In a preferred embodiment the paste forming compound is glycerol. The composition may also comprise free water at preferably 10 weight % or less of free water of the total content of the composition, or more preferably 8 weight % or less of free water, or even more preferably 5 weight % or less of free water but preferably 1 weight % or more, more preferably 2 weight % or more, even more preferably 3 weight % or more.

Glycerol is a preferred paste forming compound since it is widely used and generally accepted as ingredient in pharmaceutical, cosmetic and personal care products. It is easily soluble in water and has a high boiling point and may in the process described in the present invention, by selecting an appropriate drying temperature, be selectively retained in the composition while excess free water is evaporated. Further, glycerol has hygroscopic properties which are believed to aid in extracting free water found in the vicinity of the particles, thus increasing the stability of the particles. The affinity of water to glycerol further allows for some free water to remain in the composition without significantly compromising the shelf life, in turn facilitating preparation of a composition with high particle content that still has favorable viscosity and makes the preparation process easier and more economic since less free water needs to be removed.

Amorphous calcium phosphate is a metastable phase that tends to crystallize into more stable forms of calcium phosphate such as octacalcium phosphate or hydroxyapatite. The amorphous calcium phosphate particles according to the present invention are stabilized by magnesium substitution but may still crystallize over time in ambient conditions depending on temperature and humidity. The compositions with particles and paste forming compound according to the present invention can enable long-term stability of the particles.

The composition or the particle-containing product formulation of the present invention preferably has a very limited amount of free water, such as <10 weight %. Some free water associated to glycerol may remain in the composition even after drying. Excess amounts of free water may degrade the particles which then may form smaller particles with a higher tendency to crystallize. This process of particle degradation and crystallization is essential for the particles' bioactive properties that result in mineralization and occlusion of dentin tubules and should hence be preserved preferably until they have reached the site of treatment or when in contact with saliva and dentin liquor in the oral cavity and dentin surface. However, a composition completely free of water is also not desirable since it will be too thick to work properly in a toothpaste or similar. By having a small amount of free water in the composition or the particle containing product formulation, such as <10 weight % but >1 weight %, the composition has a good flowability while still maintaining a stability of the particles, i.e. they remain XRD amorphous for 18 months or more. In one embodiment the amount of free water in the composition is 10 weight % or less of the total content of the composition or the formulation, or more preferably 8 weight % or less of free water, or even more preferably 5 weight % or less of free water but preferably 1 weight % or more, more preferably 2 weight % or more, even more preferably 3 weight % or more.

The composition or the particle-containing product formulation may preferably further contain additives such as fluoride, potassium, hydrogen peroxide or carbamide peroxide, xylitol, xantham gum, flavors like menthol, polymer thickeners or preservatives. Fluoride is preferred since it strengthens the teeth. Potassium is a preferred nerve depolarizer. Hydrogen peroxide and carbamide peroxide are preferred teeth bleaching agents.

In the composition the particles are preferably present in an amount or concentration of 1 to 50 weight %. The amount should be adjusted so that the viscosity, homogeneity and handling properties of the composition is sufficient to make sure that the particles are well dispersed and do not agglomerate. The particle concentration in the composition should preferably be high as to maximize value per unit volume, but not so high such that the viscosity increases to levels that impede normal handling or homogenization. In a preferred embodiment the amount of particles in the composition is 25-50 weight %. In another preferred embodiment the amount is 35-45 weight % more preferably around 40 weight %. The amount or concentration of the paste forming compound is preferably at least 50 weight %, more preferably at least 55 weight %. In one preferred embodiment the concentration of the paste forming compound is 55-65 weight % preferably around 60 weight %. In one preferred embodiment the composition comprises 35-45 weight % preferably around 40 weight % particles, 50-60 preferably around 55 weight % glycerol, and 3-8 weight % preferably around 5 weight % free water.

The paste forming compound, the presence of magnesium and the method by which the particles and paste forming compound are mixed and dried to form a composition are of importance to the long-term stability and shelf life of the particles. The present inventors have demonstrated that the particles in compositions of the present invention are long-term stable in both ambient and accelerated conditions, see Examples 24 and 25. Ambient conditions refer to room temperature (20-25° C.), and accelerated conditions refer to 40° C.

The composition may be used to prepare a particle-containing product formulation such as a dental or oral care product. A dental or oral care product such as toothpaste, desensitizing gel, bleaching paste or gel, dental varnish, prophy paste or sealant preferably contains 0.5-15 weight % of particles according to the present invention, and some paste forming compound and additives. The concentration of the paste forming compound will vary between different particle-containing product formulations in order to provide particle-containing product formulations with good handling properties such as viscosity, homogeneity and spreadability for the different applications. In a preferred embodiment for a desensitizing gel the concentration of the particles is 5-9 weight % more preferably 6-8 weight %, more preferably around 7.5 weight %. The concentration of the paste forming compound is preferably 50-90 weight %, more preferably 60 to 85 weight %, more preferably 70-80 weight % in order to provide a product with good handling properties such as viscosity, homogeneity and spreadability.

The long-term stability of particle-containing product formulations is important to ensure adequate product shelf life. For example, it may be important that the appearance of the particles and the consistency of the composition is essentially maintained as well as that the particles remain XRD amorphous during the storage. The present inventors have demonstrated that a desensitizing gel containing particles and additives according to the present invention is stable in both ambient and accelerated conditions for extended time periods, see Examples 26 and 27. A desensitizing gel preferably contains 5-9 weight % of the particles. In a preferred embodiment the desensitizing gel contains 6 weight % or more, or 7 weight % or more but preferably 8 weight % or less or about 7.5 weight % of the particles.

A toothpaste preferably contains 0.5-6 weight % of the particles. In a preferred embodiment the toothpaste contains 0.5 weight % or more, or 1 weight % or more of the particles but preferably 5 weight % or less, or 4 weight % or less, or 3 weight % or less.

A varnish, a prophy paste or a sealant preferably contains 5-15 weight % of the particles. In a preferred embodiment the varnish, prophy paste or sealant contains 6 weight % or more, or 8 weight % or more, or 10 weight % or more of the particles but preferably 13 weight % or less, or 11 weight % or less.

Figure 4:
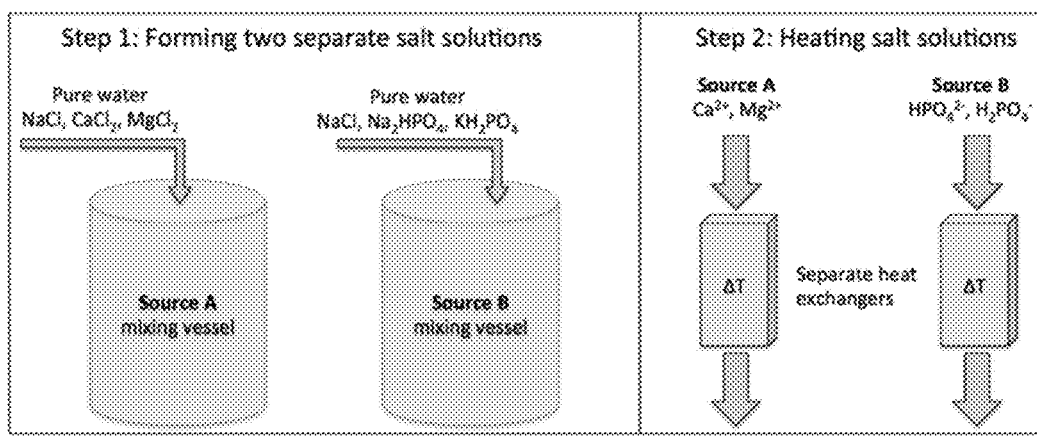
FIG. 4. Schematic illustration of the method according to the present invention, steps 1 and 2.
Figure 5:
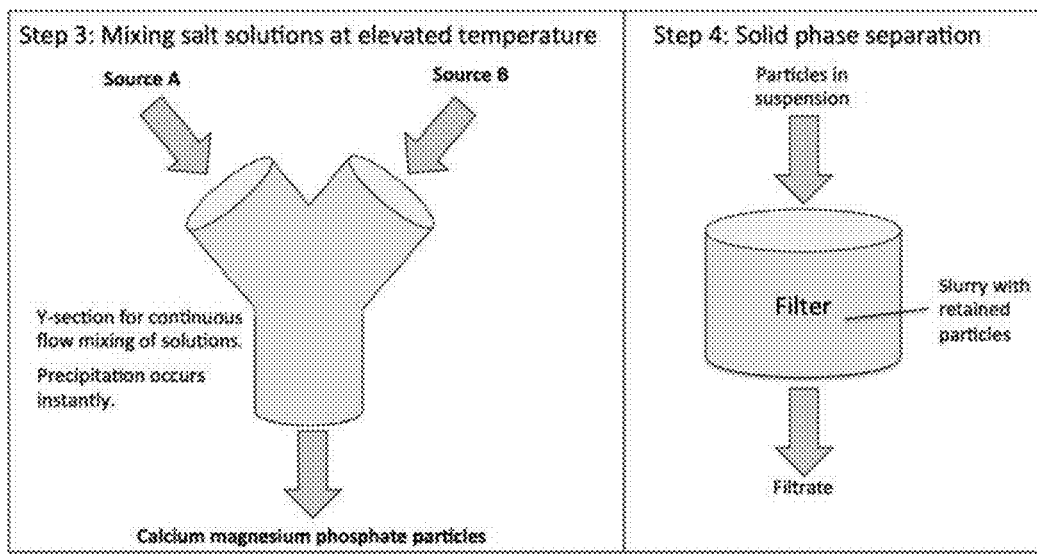
FIG. 5. Schematic illustration of the method according to the present invention, steps 3 and 4.

Turning now to FIGS. 4 to 5 disclosing the general method of preparing the spherical and hollow particles according to the present invention where step 1 schematically represents point a-b in the claimed method, step 2 represents point c, step 3 represents point d-e and step 4 represents point f.

In a first step a first aqueous solution is provided having a pH of 6 to 10, preferably 7 to 10, more preferably 7 to 8, and where the solution has a first temperature. The first aqueous solution comprises dihydrogen phosphate ions and/or hydrogen phosphate ions, counter ions and optionally additional ions. The counter ions are preferably sodium and/or potassium ions. Additional ions may be selected from sodium, potassium, chloride, silicon, zinc and fluoride or combinations thereof. The molar ratio of $H_2PO_4:HPO_4$ in the first aqueous solution is preferably in the range of 0-100: 75-600 more preferably 1-2:4-6. In a preferred embodiment the concentration of dihydrogen phosphate is 0 to 100 mM or more preferably 20 to 80 mM. Hydrogen phosphate has preferably a concentration in the first aqueous solution of 30 to 300 mM more preferably 80 to 250 mM. The total concentration of phosphate in the first aqueous solution is preferably 60 to 800 mM.

A second aqueous solution is also provided having a second temperature and comprises calcium and magnesium ions, counter ions and optionally additional ions. The counter ions are preferably chloride, sodium and/or potassium ions. Additional ions may be selected from sodium, potassium, chloride, silicon, zinc and fluoride or combinations thereof. The concentration of calcium in the second aqueous solution is preferably 10-200 mM and the concentration of magnesium is preferably 5 to 120 mM. In a preferred embodiment the calcium concentration is 20-100 mM, more preferably 30-70 mM. In another preferred embodiment the magnesium content is 10-60 mM more preferably 12-40 mM. Calcium is preferably in molar excess to magnesium in the second aqueous solution. The molar ratio of calcium to magnesium is preferably 4:1 to 1.05:1 more preferably 2:1 to 4:3 or more preferably around 5:3.

In one preferred embodiment the amount of phosphate in the first aqueous solution is in molar excess to the total amount of calcium and magnesium in the second aqueous solution. In a preferred embodiment the molar ratio between phosphate and calcium and magnesium ($PO_4:(Ca+Mg)$) is 1.5:1 or higher, preferably 2:1 or higher. In another preferred embodiment the molar ratio is 2:1 to 6:1 or more preferably 2.2:1 to 5:1.

The first aqueous solution and the second aqueous solution has individually a first and second temperature of preferably 10-35° C. respectively more preferably 20-30° C., more preferably 20-25° C. The water in the first and second aqueous solution may be tap water or preferably purified water more preferably deionized, distilled, double distilled or ultra-pure water. Even though the present invention is described to use two aqueous solutions, a first and a second aqueous solution, the skilled person understands that the first and second aqueous solution may actually each be two or more aqueous solutions or sub-solutions.

At least one of the two aqueous solutions, the first and/or the second aqueous solutions, is then heated to a first and second elevated temperature respectively. In one embodiment both the first and the second aqueous solution are heated to a first and second elevated temperature respectively. In FIG. 4 (right hand side) both solutions are heated using heat exchangers but any suitable heating device may be used. This step of heating is, without being bound by theory, believed to be important for the formation of nano bubbles (long-lasting gas-containing cavities) in electrolyte solutions onto which the ions of the two solutions precipitate and forms the hollow structure of the particles of the present invention when the two solutions are brought into contact. The heating of at least one of the two solutions should result in an individual temperature increase of preferably at least 40° C., more preferably at least 50° C. In other words, a first and second temperature difference between the first/second temperature and the first/second elevated temperature respectively. In a preferred embodiment the first temperature difference is 40-80° C., preferably 50-70° C. In another preferred embodiment the second temperature difference is 40-80° C., preferably 50-70° C. The first and second elevated temperature is then individually preferably at least 60° C., more preferably 70-90° C.

The two solutions, where at least one has been heated, are then brought into contact with each other resulting in a third aqueous solution having a third temperature (FIG. 5, step 3). This may be done by adding one of the solutions to the other preferably adding the second solution to the first solution but preferably the two solutions are brought into contact in a continuous manner and preferably in a continuous flowing manner. By bringing them into contact in a continuous flowing manner facilitates a more efficient production, makes it easier to scale up the output of formed particles and provides better control of the method. In one embodiment the two solutions (first and second aqueous solutions) are brought into contact in a manifold or a three way manifold preferably in a Y-shaped manifold (Y-section) as schematically illustrated in FIG. 5 (left hand side). Precipitation will occur more or less instantly (<10 seconds) when the two solutions are brought into contact with each other and the precipitation is allowed to continue for a suitable period of time depending on both practical constraints as well as targeted minor adjustments to desired properties, but typically for 1-600 seconds.

The continuous flow process in which the two solutions are mixed may continue provided that the starting solutions are replenished, allowing for continuous retrieval of formed particles. The amount of phosphate is in molar excess to the total amount of calcium and magnesium ($PO_4$>(Ca+Mg)) when the first and second solutions are brought into contact. Without being bound by theory an excess of phosphate to the total amount of calcium and magnesium in the third aqueous solution will increase the buffering capacity which in turn limits the formation of crystalline calcium phosphate phases, see Example 12. In a preferred embodiment the molar ratio between phosphate and calcium and magnesium ($PO_4$:(Ca+Mg)) in the third aqueous solution is 1.5:1 or higher, preferably 2:1 or higher. In another preferred embodiment the molar ratio is 2:1 to 6:1 or more preferably 2.2:1 to 5:1. In a preferred embodiment calcium is in molar excess to magnesium in the third aqueous solution. The molar ratio of calcium to magnesium is preferably 4:1 to 1.05:1 more preferably 2:1 to 4:3 or more preferably around 5:3.

In one preferred embodiment the third temperature is 70-95° C., more preferably 80-85° C. since the mass yield of the reaction is higher and at temperatures of >100° C. the degree of crystallization increases, see Example 16. When bringing the first and the second aqueous solution into contact the volume ratio between the first and the second aqueous solution is preferably 2:1 to 1:2, preferably 1.10:1 to 1:1.10 or preferably 1.05:1 to 1:1.05 or more preferably 1:1.

A suspension of precipitated particles and an aqueous solution is formed and precipitated particles are then isolated and/or collected using any suitable technique. Preferably the isolation and/or collection is done using a suitable filtration technique, centrifugation and/or sedimentation and decantation. The isolated and/or collected particles are preferably then washed using any suitable solvent such as water or alcohols. It is preferred that the washing is done using purified water more preferably deionized, distilled, double distilled or ultra-pure water. The washing may preferably be done at a fourth temperature of 50-90° C., more preferably 70-80° C. In order to make sure that the particles are clean and free from unwanted ionic residues the washing step may be repeated. The isolated and/or collected and washed particles may then be dewatered or partially dewatered preferably with centrifugation or more preferably at an increased temperature and/or at reduced pressure. In a preferred embodiment the dewatering/partial dewatering or drying is done at a fifth temperature of at least 50° C. preferably 50-150° C., more preferably 60-110° C., more preferably 60-80° C. or around 80° C. The dewatering or partial dewatering is preferably conducted until a slurry containing 70-90 weight % free water is obtained, more preferably 75-85 weight %. At this stage the particles are still well suspended and evenly dispersed in the slurry and the slurry may easily be mixed with a paste forming compound to form a wet composition essentially free from any agglomerates. Dewatering the slurry further or drying the particles completely at this stage results in formation of larger particle agglomerates which are increasingly difficult to mix and homogeneously suspend in the paste forming compound to obtain a smooth and free flowing composition. The present inventors found that when mixing dry or essentially dry isolated particles with a paste forming compound it is essentially impossible to obtain an equally homogeneous, smooth and free flowing composition, even when using finely milled and sieved powder. Avoiding drying and milling to form a fine powder for dispersion in the paste forming compound or product formulation also reduces health and safety risks associated with powder handling.

Drying the particles without the presence of a paste forming compound may also inadvertently increase the degree of crystallinity, and drive formation of harder particles that may require high energy to disperse, in turn risking the integrity of the particles. Stability of the particles according to the present invention is limited when stored as a fine powder in ambient conditions, see Example 30, which further highlights the significance of forming a composition with a paste forming compound already at the manufacturing stage.

In one embodiment, should it be wanted despite the cited drawbacks, the formed, isolated and optionally washed and/or dewatered particles are further dried at a sixth temperature, preferably 50-150° C. more preferably 60-110° C. to form a powder.

Figure 6A:
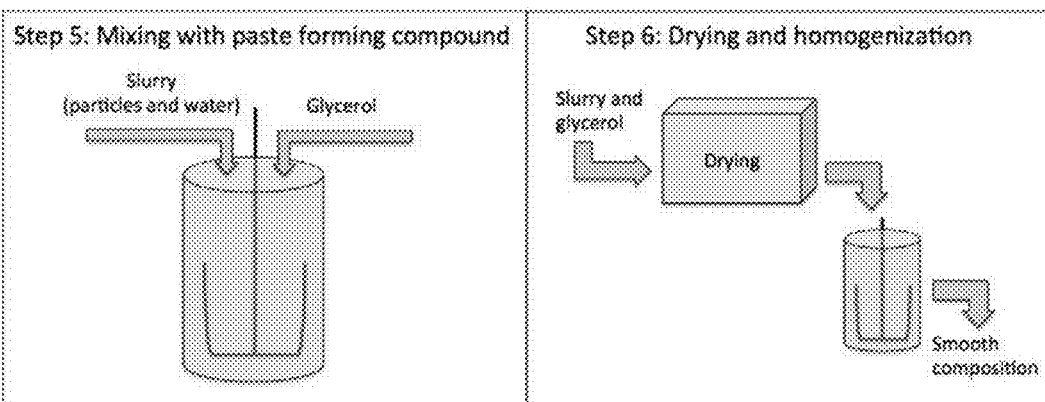
FIG. 6. a) schematic illustration of the method according to the present invention, steps 5 and 6, and b) flow-chart of a method according to the present invention.

Turning now to FIG. 6a which schematically illustrates the preparation of the composition of the present invention. Preparing the composition of the present invention is done by preparing the particles according to the present invention and mixing the particles with the paste forming compound. Mixing the particles with the paste forming compound is preferably done after partial dewatering of the particles i.e. in a state in which the particles are still suspended and preferably homogeneously distributed in a slurry. The slurry before mixing with the paste forming compound comprises preferably 10-30 weight % particles and 70-90 weight % water, more preferably 15-25 weight % particles and 75-85 weight % water. The paste forming compound is preferably selected from glycerol, triglyceride, polyethylene glycol, propylene glycol, polypropylene glycol, polyvinyl alcohol, mineral oil or liquid paraffin. In a preferred embodiment the paste forming compound is glycerol. In a preferred embodiment the paste forming compound is essentially free from water, such as <10 weight % of water.

The obtained composition of particles, free water and paste forming compound is preferably dewatered in order to remove as much free water as possible and form a stable and homogeneous composition with long term stability. In one embodiment the amount of free water is less than 10 weight %, preferably less than 5 weight %, more preferably less than 3 weight % water. Having a small amount of water left in the composition may aid in forming a smooth and homogeneous composition with suitable viscosity. In one preferred embodiment the amount of free water in the composition is 0.1 weight % or more, or 0.5 weight % or more, or 1 weight % or more, but preferably 8 weight % or less, or 5 weight % or less. The dewatering of the obtained mixture of spherical and hollow particles and paste forming compound is preferably done at a seventh temperature and/or a reduced pressure where the seventh temperature is preferably in the range of 50-150° C., more preferably 60-90° C. The reduced pressure is preferably 500 mbar or lower. It is preferred that this mixture is homogenized during and/or after dewatering preferably by mechanical means to form a smooth composition.

Figure 6B:
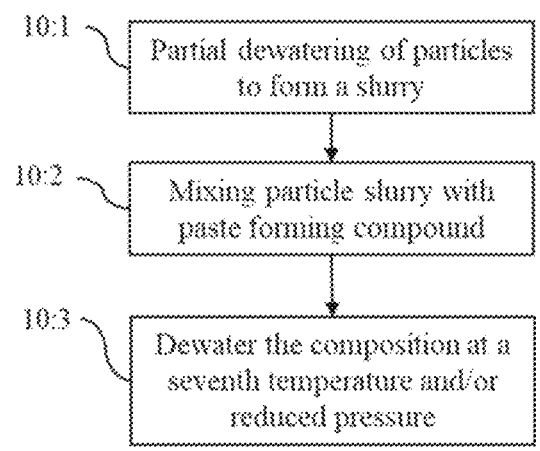

The obtained mixture may for example be homogenized using mechanical homogenizing equipment like a rotor-stator homogenizer for 1 to 30 minutes. The preparation of the composition is schematically summarized in FIG. 6b. As illustrated the process comprises at least three steps:

10:1: Partial dewatering of the ACP particles that has been prepared as described above, the particles are dewatered until they form a slurry that comprises 10-30 weight % particles and 70-90 weight % water;

10:2 Mixing of the particle containing slurry with a paste forming compound until a homogenous mixture; and 10:3 Dewatering the composition formed in step 10:2 at either a seventh temperature and/or at a reduced pressure until the amount of water is 8 weight % or less, or 5 weight % or less, or 2 weight % or less.

The hygroscopic properties of glycerol can make it an effective preservative of the amorphous calcium magnesium phosphate particles according to the present invention. It is advantageous with a composition comprising glycerol that even in a case when it comprises an excess of free water the ACP particles may remain XRD amorphous during storage, see Example 28.

Teeth bleaching or whitening is common practice in modern cosmetic dentistry and typically uses hydrogen peroxide or carbamide peroxide to remove stains and enhance the appearance and whiteness of teeth. Different markets currently allow for different strengths of peroxide to be applied in whitening products, but a typical formulation for take-home products contains 16% carbamide peroxide, equivalent to 5-6% hydrogen peroxide. A common side effect of teeth whitening is increased tooth sensitivity, and the enamel may be softened by the treatment resulting in reduced tooth strength. It is therefore of interest to provide effective whitening products and treatments which can also reduce tooth sensitivity and increase the hardness of enamel by mineralization. It can therefore be an advantage that a composition according to the present invention does not negatively influence the bleaching process of a teeth whitening product, as indicated in Example 29.

EXAMPLES

Example 1

A first aqueous solution was prepared with concentrations 125 mM NaCl, 160 mM $Na_2HPO_4$, and 30 mM $KH_2PO_4$ (pH 7.4), and a second aqueous solution was prepared with concentrations 125 mM NaCl, 25 mM $CaCl_2$, and 15 mM $MgCl_2$, according to step 1 in FIG. 4. The two solutions were heated separately from room temperature to 85° C. via plate heat exchangers according to step 2 in FIG. 4, then flow mixed at a 1:1 volume ratio according to step 3 in FIG. 5 to form a precipitation at 85° C. The precipitation was collected by filtration according to step 4 in FIG. 5 using a fine mesh filter cloth, then washed using deionized water at 70° C., followed by partial dewatering using vacuum. The slurry, containing approximately 20 weight % precipitated particles and 80 weight % water, was mixed with glycerol according to step 5 in FIG. 6 to form a homogeneous mixture with a dry weight ratio 2:3 of particles and glycerol. The mixture was then dried in a forced convection oven at 80° C. to remove water, and homogenized by mechanical means to form a smooth, viscous composition according to step 6 in FIG. 6. Dry content of the composition was 98 weight %.

The formed particles were spherical in shape, consisting of a porous shell and a hollow interior. Individual spheres diameters were in the range 100-300 nm, whereas clusters and formations of fused spheres were in the range 200-500 nm. Representative scanning electron microscope (SEM) images of the particles are shown in FIG. 1.

XRD analysis of the particles revealed that they were amorphous. No characteristic peaks were present, only a broad increase in intensity around 2Theta=30° suggesting presence of amorphous calcium phosphate, see FIG. 2.

Elemental analysis of the particles was determined by inductively coupled plasma optical emission spectroscopy (ICP-OES), and demonstrated contents are shown in Table 1. Assuming that all P is present as $PO_4$, the calculated content of $PO_4$ is also shown in the table, along with Ca/P and (Ca+Mg)/P molar ratios. The measured values of Ca and Mg combined with the calculated value of $PO_4$ amounts to 86 weight %, resulting in an approximated amount of 14 weight % bound $H_2O$. Based on the data in the example a balanced chemical formula for the particles is proposed as:

$Ca_{2.7}Mg_{1.3}H(PO_4)_3*4H_2O$

TABLE 1

Results of ICP-OES elemental analysis of the formed particles.

| Measured values | | | Calculated | | |
|---|---|---|---|---|---|
| Ca | Mg | P | value $PO_4$ | Molar ratios | |
| (wt %) | (wt %) | (wt %) | (wt %) | Ca/P | (Ca + Mg)/P |
| 22 | 6 | 19 | 58 | 0.9 | 1.3 | wt % denotes weight %.

The particle size distribution was determined by DLS after suspending the formed particles in ethanol and dispersing aggregated particles using ultrasound. The z-average particle size was 370 nm and the distribution by number is shown in FIG. 3.

Surface area of the material was 24 m²/g as determined BET method using nitrogen gas.

Example 2

A first aqueous solution was prepared with concentrations 500 mM NaCl, 640 mM $Na_2HPO_4$, and 119 mM $KH_2PO_4$ (pH 7.4). A second aqueous solution was prepared with concentrations 500 mM NaCl, 100 mM $CaCl_2$, and 60 mM $MgCl_2$. The two solutions were heated separately to 85° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 3

A first aqueous solution was prepared with 100 mM NaCl, 128 mM $Na_2HPO_4$, and 24 mM $KH_2PO_4$ (pH 7.4). A second aqueous solution was prepared with 100 mM NaCl, 20 mM $CaCl_2$, and 12 mM $MgCl_2$. The two solutions were heated separately to 70° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 4

A first aqueous solution was prepared with 100 mM NaCl, 128 mM $Na_2HPO_4$, and 24 mM $KH_2PO_4$ (pH 7.4). A second aqueous solution was prepared with 100 mM NaCl, 20 mM $CaCl_2$, and 12 mM $MgCl_2$. The two solutions were heated separately to 80° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 5

A first aqueous solution was prepared with 100 mM NaCl, 128 mM $Na_2HPO_4$, and 24 mM $KH_2PO_4$ (pH 7.4) A second aqueous solution was prepared with 100 mM NaCl, 20 mM $CaCl_2$, and 12 mM $MgCl_2$. The two solutions were heated separately to 90° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 6

A first aqueous solution was prepared with 160 mM $Na_2HPO_4$, and 30 mM $KH_2PO_4$ (pH 7.4). A second aqueous solution was prepared with 50 mM $CaCl_2$, and 30 mM $MgCl_2$. The two solutions were heated separately to 85° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 7

A first aqueous solution was prepared with 100 mM NaCl and 150 mM $KH_2PO_4$ (pH 4.7). A second aqueous solution was prepared with 100 mM NaCl, 20 mM $CaCl_2$, and 12 mM $MgCl_2$. The two solutions were heated separately to 85° C., and then mixed at a 1:1 volume ratio to form a precipitation. The precipitation was collected by filtration, washed and analyzed by SEM and XRD. The precipitated particles were rounded but not spherical. The particles had rough surface features and did not appear hollow. XRD analysis demonstrated that the particles were crystalline whitlockite, a magnesium substituted form of tricalcium phosphate (TCP).

Example 8

A first aqueous solution was prepared with 100 mM NaCl, 75 mM $Na_2HPO_4$, and 75 mM $KH_2PO_4$ (pH 6.4). A second aqueous solution was prepared with 100 mM NaCl, 20 mM $CaCl_2$, and 12 mM $MgCl_2$. The two solutions were heated separately to 85° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 9

A first aqueous solution was prepared with 100 mM NaCl, 145 mM $Na_2HPO_4$, and 4.8 mM $KH_2PO_4$ (pH 8.1). A second aqueous solution was prepared with 100 mM NaCl, 20 mM $CaCl_2$, and 12 mM $MgCl_2$. The two solutions were heated separately to 85° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 10

A first aqueous solution was prepared with 75 mM $Na_2HPO_4$ (pH 9.3). A second aqueous solution was prepared with 20 mM $CaCl_2$ and 12 mM $MgCl_2$. The two solutions were heated separately to 85° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 11

A first aqueous solution was prepared with 190 mM $Na_2HPO_4$ (pH 9.4). A second aqueous solution was prepared with 50 mM $CaCl_2$, and 30 mM $MgCl_2$. The two solutions were heated separately to 85° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

Example 12

A first aqueous solution was prepared with 60 mM $Na_2HPO_4$ (pH 9.3). A second aqueous solution was prepared with 50 mM $CaCl_2$, and 30 mM $MgCl_2$. The two solutions were heated separately to 85° C., and then mixed at a 1:1 volume ratio to form a precipitation. The precipitation was collected by filtration, washed and analyzed by SEM and XRD. The collected particles were not spherical and not hollow, but consisted of irregular and seemingly dense particles with a rough surface. XRD analysis of the material demonstrated that the crystalline phase was whitlockite. This result is in line with the type of particles formed at low pH, demonstrated in Example 7. The difference with this Example is that initial pH of the phosphate solution was high, but that $HPO_4^{2-}$ was not in excess in relation to $Ca^{2+}$ and $Mg^{2+}$ content, resulting in the following reaction:

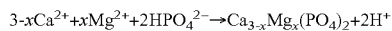
$$3\text{-}xCa^{2+}+xMg^{2+}+2HPO_4^{2-}\rightarrow Ca_{3-x}Mg_x(PO_4)_2+2H^+$$

Without an excess of $HPO_4^{2-}$ the system will lose its buffering capacity and the product $H^+$ will lower pH and promote formation of crystalline particles of TCP, which has a higher Ca/P ratio than the particles formed and characterized in Example 1.

Example 13

A first aqueous solution was prepared with 220 mM $Na_2HPO_4$ (pH 9.4). A second aqueous solution was prepared with 60 mM $CaCl_2$, and 36 mM $MgCl_2$. The two solutions were heated separately to 85° C., and then mixed at a 1:1 volume ratio to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2. The pH of the filtrate was 7.0, indicating that $HPO_4^{2-}$ was in sufficient excess to maintain neutral pH.

This example resulted in twice the mass of particles as Example 1.

precipitation was collected by filtration, washed and analyzed by SEM and XRD. The formed particles were a mixture of spherical particles and fine crystallites, identified by XRD as brushite ($CaHPO_4*2H_2O$).

In a second experiment, the two solutions were heated separately to 65° C. The first solution (phosphate) was then admixed to the second solution (calcium and magnesium) at equal volume to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2.

In a third experiment, the two solutions were heated separately to 85° C. The first solution (phosphate) was then admixed to the second solution (calcium and magnesium) at equal volume to form a precipitation. The precipitation was collected by filtration, washed and analyzed by SEM and XRD. The formed particles were similar in shape, size, and appearance as particles shown in FIG. 1, and were XRD amorphous similar to the pattern shown in FIG. 2. Compared to the experiment at 65° C., the mass yield of the reaction was increased at 85° C.

This experimental series demonstrates that there is a preferred temperature window in which the precipitation reaction is stable and effective in terms of consistency of shape, size, and appearance and mass yield.

Example 15

A first aqueous solution was prepared with 0.5 mM KCl, 200 mM NaCl, 16 mM $Na_2HPO_4$, and 3 mM $KH_2PO_4$ (pH 7.4). A second aqueous solution was prepared with 0.5 mM

TABLE 2

Summary table with process parameters and compositions used for synthesis of particles in Examples 1-13.

| Ex # | Temp. (° C.) | Phosphate solution pH | NaCl (mM) | CaCl$_2$ (mM) | MgCl$_2$ (mM) | Na$_2$HPO$_4$ (mM) | KH$_2$PO$_4$ (mM) | Spher. part. (SEM) | Amorph. (XRD) |
|---|---|---|---|---|---|---|---|---|---|
| 1 | 85 | 7.4 | 125 | 25 | 15 | 160 | 30 | Yes | Yes |
| 2 | 85 | 7.4 | 500 | 100 | 60 | 640 | 119 | Yes | Yes |
| 3 | 70 | 7.4 | 100 | 20 | 12 | 128 | 24 | Yes | Yes |
| 4 | 80 | 7.4 | 100 | 20 | 12 | 128 | 24 | Yes | Yes |
| 5 | 90 | 7.4 | 100 | 20 | 12 | 128 | 24 | Yes | Yes |
| 6 | 85 | 7.4 | 0 | 50 | 30 | 160 | 30 | Yes | Yes |
| 7 | 85 | 4.7 | 100 | 20 | 12 | 0 | 150 | No | No |
| 8 | 85 | 6.4 | 100 | 20 | 12 | 75 | 75 | Yes | Yes |
| 9 | 85 | 8.1 | 100 | 20 | 12 | 145 | 4.8 | Yes | Yes |
| 10 | 85 | 9.3 | 0 | 20 | 12 | 75 | 0 | Yes | Yes |
| 11 | 85 | 9.4 | 0 | 50 | 30 | 190 | 0 | Yes | Yes |
| 12 | 85 | 9.3 | 0 | 50 | 30 | 60 | 0 | No | No |
| 13 | 85 | 9.4 | 0 | 60 | 36 | 220 | 0 | Yes | Yes |

In the Result columns: Spher.part denotes spherical particles, and Amorph. denotes amorphous.

Example 14

A first aqueous solution was prepared with 0.5 mM KCl, 200 mM NaCl, 16 mM $Na_2HPO_4$, and 3 mM $KH_2PO_4$. A second aqueous solution was prepared with 0.5 mM KCl, 200 mM NaCl, 2.5 mM $CaCl_2$, and 1.5 mM $MgCl_2$.

In a first experiment, the two solutions were heated separately to 45° C. The first solution (phosphate) was then admixed to the second solution (calcium and magnesium) at equal volume to form a precipitation, i.e. in an alternative way compared to step 2 and 3 in FIGS. 4 and 5. The KCl, 200 mM NaCl, 2.5 mM $CaCl_2$, and 0.75 mM $MgCl_2$. The two solutions were heated separately to 85° C. The first solution (phosphate) was then admixed to the second solution (calcium and magnesium) at equal volume to form a precipitation. The precipitation was collected by filtration, washed and analyzed by SEM and XRD. There were no spherical particles present, but formation of a poorly crystalline phase identified as whitlockite in XRD.

In a second experiment, a first aqueous solution was prepared with 0.5 mM KCl, 200 mM NaCl, 16 mM $Na_2HPO_4$, and 3 mM $KH_2PO_4$. A second aqueous solution was prepared with 0.5 mM KCl, 200 mM NaCl, and 2.5 mM $CaCl_2$. The two solutions were heated separately to 85° C. The first solution (phosphate) was then admixed to the second solution (calcium) at equal volume to form a precipitation. The precipitation was collected by filtration, washed and analyzed by SEM and XRD. There were no spherical particles present, but formation of flake-like crystals identified as tricalcium phosphate (TCP) in XRD.

These experiments demonstrate that magnesium acts as a stabilizer of the amorphous phase, and that a sufficient degree of magnesium substitution is required to retain the amorphous phase.

Example 16

A microwave synthesizer was used to evaluate an alternative heating method and extended process temperature range. For the experiments, a single solution was prepared with 0.5 mM KCl, 200 mM NaCl, 16 mM $Na_2HPO_4$, 3 mM $KH_2PO_4$, 2.5 mM $CaCl_2$, and 1.5 mM $MgCl_2$. In different experiments, the solution was placed in a sealed glass vial and rapidly (<2 minutes) brought from room temperature (23° C.) to 50, 70, 90, 100, 120, or 140° C. using microwave assisted heating. The resulting precipitates were analyzed by SEM, which revealed that spherical and hollow particles had formed in all instances, comparable to particles shown in FIG. 1. At temperatures at or above 100° C., the particles had slightly rougher surface features and demonstrated signs of crystallization.

The experiments demonstrate that alternative means of heating can be used to synthesize the particles, and that the particles can be synthesized in a wide temperature window depending on the means of heating.

Example 17

Figure 7:
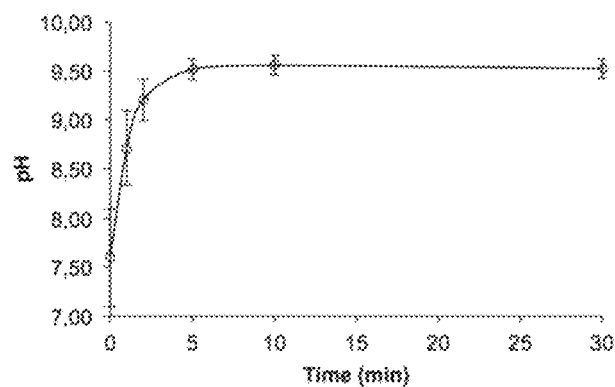
FIG. 7. pH buffering capacity of the calcium magnesium phosphate particles according to the present invention.

A composition containing 40 weight % spherical and hollow calcium magnesium phosphate particles and 60 weight % glycerol according to the present invention was admixed to deionized water to evaluate pH-buffering capability. In the experiment 0.5 g of the composition was added to 500 mL water resulting in a concentration of 0.1 weight %. The pH of the solution was monitored during the first 30 minutes of dissolution of the composition, and the result is shown in FIG. 7. By adding the composition, pH of the solution increased sharply from approximately 7.5 to 9.5 within 5 minutes, after which it was stable.

This rapid release of ions is an important feature for certain dental materials and products. A local increase in pH is beneficial for remineralization of enamel and dentin, as it promotes nucleation and growth of hydroxyapatite.

Example 18

Figure 8:
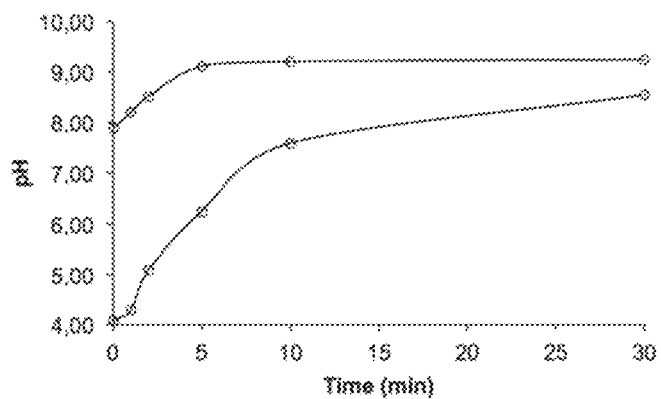
FIG. 8. pH buffering capacity of a desensitizing gel containing calcium magnesium phosphate particles according to the present invention.

A desensitizing gel containing 7.5 weight % spherical and hollow calcium magnesium phosphate particles according to the present invention was admixed to aqueous solutions at pH 4 and pH 7.9 in the concentration 0.1 weight %. The pH of starting solutions was adjusted using 0.1 M HCl and 0.1 M NaOH, respectively. The pH of the solutions was monitored during the first 30 minutes of dissolution of the gel, and the results are shown in FIG. 8. It was demonstrated that the gel raised pH in both instances, from pH 4.0 to 8.6, and from pH 7.9 to pH 9.3, respectively. A similar test performed with a corresponding gel with the calcium magnesium phosphate replaced with inert glass particles resulted in an unchanged pH, indicating that the particles caused the effect.

The desensitizing gel is intended as a treatment option for dentin hypersensitivity by remineralizing exposed dentin tubules. The increase in pH by the particles will facilitate nucleation and growth of hydroxyapatite mineral on the dentin surface and inside exposed dentin tubules.

Example 19

Figure 9:
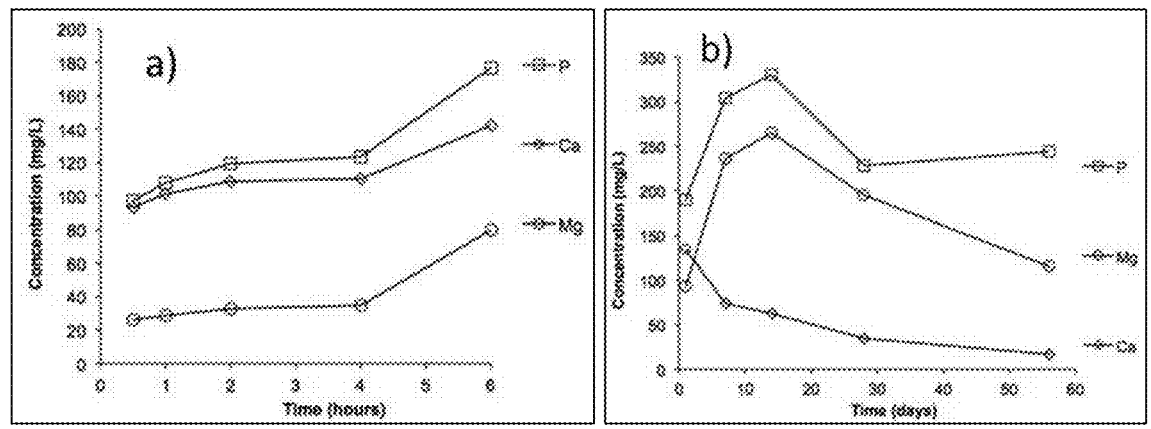
FIG. 9. Ion release profiles of Ca, Mg, and P from the calcium magnesium phosphate particles according to the present invention. a) Release during the initial 6 h and b) continuing release followed by a decrease in ion concentrations, signifying a precipitation from the solution.

Spherical and hollow calcium magnesium phosphate particles according to the present invention were dispersed in 0.05 M Tris-HCl buffer (pH 7.4) at a concentration of 10 mg/mL, and stored at 37° C. for up to 8 weeks. The release of calcium, magnesium, and phosphate ions from the particles was monitored by filtering particles and analyzing the filtrate by ICP-OES. The filtrate was diluted prior to analysis. The results are shown in FIG. 9 and demonstrate that the release is characterized by an initial burst, followed by a decrease in ion concentrations, most pronounced for Ca. The initial burst release of ions will facilitate a rapid mineralization process, and the subsequent decrease in calcium content in the filtrate indicates that calcium phosphate was re-precipitated from solution, but with a Ca/P ratio higher than for the original particles, i.e. formation of calcium phosphate with a Ca/P ratio closer to that of hydroxyapatite.

Example 20

A gel containing 5 weight % spherical and hollow calcium magnesium phosphate particles according to the present invention was prepared for evaluation of dentin occlusion and remineralization properties. A similar gel containing 5 weight % hollow calcium phosphate particles according to previous invention (WO 2014/148997 A1) was also prepared and tested in parallel for comparison of results.

Figure 10:
FIG. 10. Dentin tubule occlusion with spherical and hollow calcium phosphate particles according to WO2014/148997A1.
Figure 11:
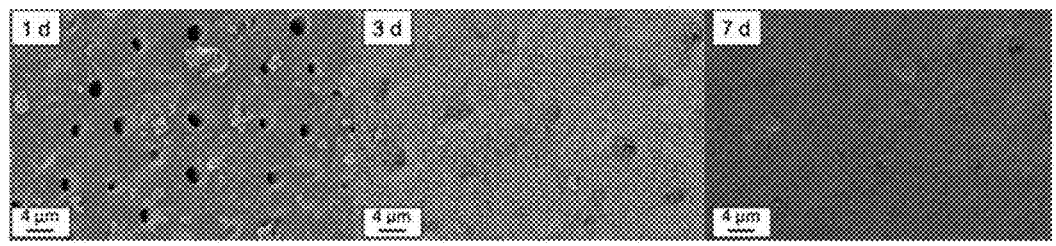
FIG. 11. Dentin tubule occlusion with spherical and hollow calcium magnesium particles according to present invention.

For the study, 1 mm thin dentin specimens were cut from extracted permanent molars of human origin and etched in phosphoric acid to expose the tubules. The gels were applied to exposed dentin surfaces twice daily by brushing with a soft bristled toothbrush for up to 7 days. The dentin specimens were stored in artificial saliva at 37° C. between brushings. After final gel application, the specimens were dried and prepared for evaluation in SEM. The appearance of dentin surfaces after 4 and 7 days treatment with the gels are shown in FIG. 10 and FIG. 11. The particles according to the present invention resulted in a faster and more complete occlusion of tubules than particles prepared according WO 2014/148997. This is credited to the smaller average diameter of the spherical particles, allowing them to more easily penetrate the tubules, as well as the amorphous character of the current particles, which allows for a more rapid dissolution and release of bioactive ions that mineralize the surface.

Example 21

A desensitizing gel formulated with 7.5 weight % spherical and hollow calcium magnesium phosphate particles according to the present invention was evaluated for dentin occlusion and remineralization properties. For the study, 1 mm thin dentin specimens were cut from extracted permanent molars of human origin and etched in phosphoric acid to expose the tubules. The dentin specimens were then brushed with the gel twice daily for one minute on each side for a total of 14 days. After each brushing sequence, samples were rinsed with deionized water and stored in artificial saliva at 37° C. until the next brushing sequence. After completion of the treatment, samples were vacuum dried and evaluated in SEM.

Figure 12:
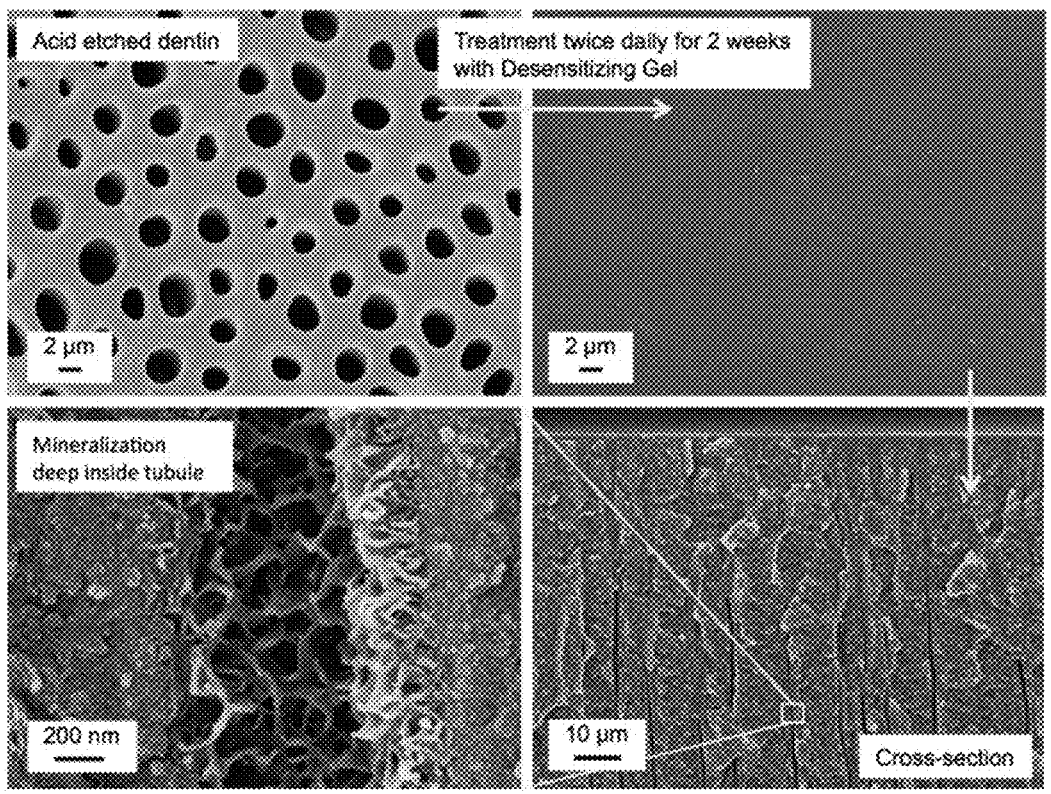
FIG. 12. Occlusion and mineralization of dentin tubules after two weeks daily treatment with a desensitizing gel, containing spherical and hollow calcium magnesium phosphate particles according to the present invention.

Result of the treatment is shown in FIG. 12, demonstrating complete occlusion of exposed dentin tubules. Evaluation of the cross section revealed that mineralization had occurred deep (>60 µm) within the tubules. The extent of occlusion achieved by the treatment makes it plausible to completely eliminate the fluid movement inside the tubules and thereby offer effective pain relief for hypersensitive teeth.

Example 22

A desensitizing gel formulated with 7.5 weight % spherical and hollow calcium magnesium phosphate particles according to the present invention was evaluated for dentin occlusion and remineralization properties when applied in combination with a fluoride toothpaste. For the study, 1 mm thin dentin specimens were cut from extracted permanent molars of human origin and etched in phosphoric acid to expose the tubules. The dentin specimens were first brushed with standard fluoride toothpaste, followed by brushing with the desensitizing gel. The sequence was repeated four times daily during four days. Dentin samples were stored in artificial saliva at 37° C. between brushings. After completion of the treatment, samples were vacuum dried and evaluated in SEM.

Figure 13:
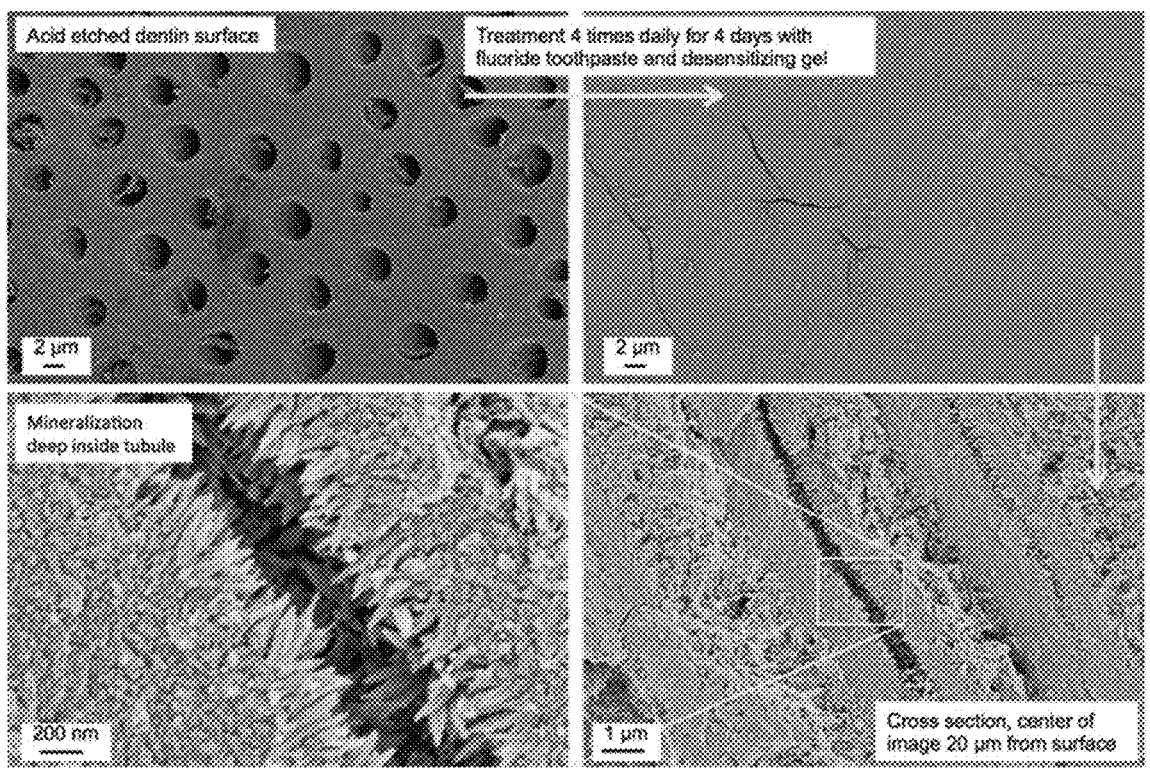
FIG. 13. SEM image. Surface and cross section of dentin disclosing occlusion and mineralization of dentin tubules after four times daily treatment for four days with fluoride toothpaste and a desensitizing gel containing spherical and hollow calcium magnesium phosphate particles according to the present invention.

Results of the treatment are shown in FIG. 13, which demonstrate that exposed tubules were completely occluded by a dense mineralized layer. Cross section evaluation of the dentin samples demonstrated that the deposited mineral inside tubules consisted of fine crystals with high aspect ratio, and that many tubules were completely occluded further than 20 µm from the dentin surface.

Example 23

Spherical and hollow calcium magnesium phosphate particles according to the present invention were stored in municipal tap water and artificial saliva at 37° C. for up to 28 days. The objective was to characterize the degradation and crystallization of the particles in different media within this time frame.

Particle samples were taken for evaluation in SEM after 7, 14, and 28 days, and for XRD evaluation after 28 days.

Figure 14:
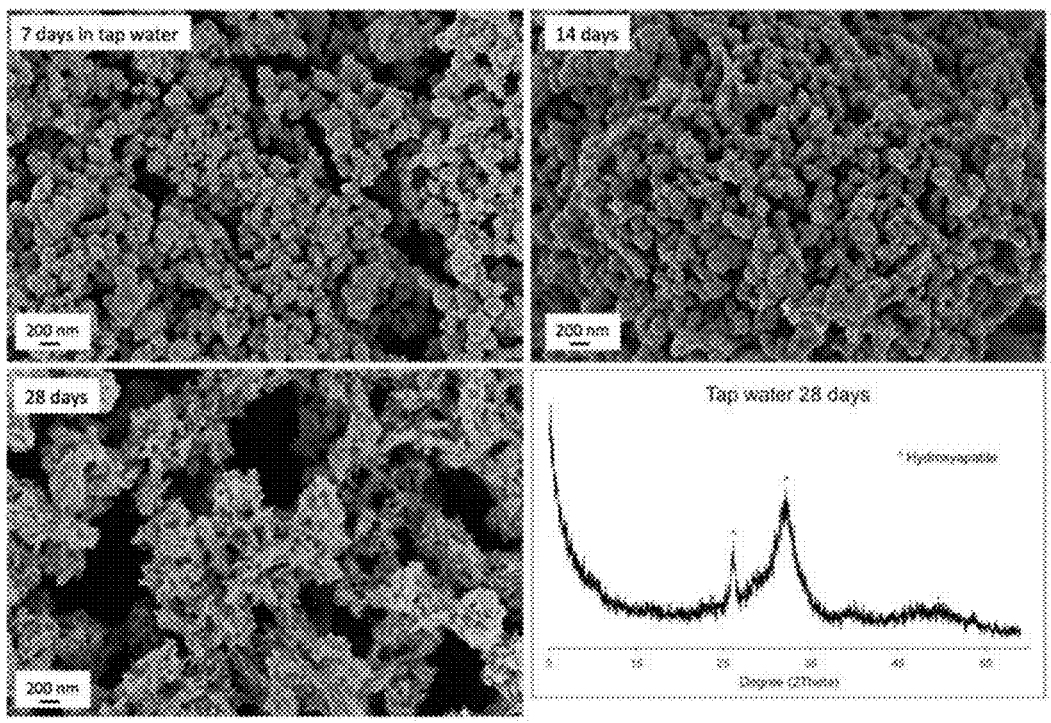
FIG. 14. SEM image and XRD pattern disclosing degradation and crystallization of calcium magnesium phosphate particles according to the present invention in tap water.
Figure 15:
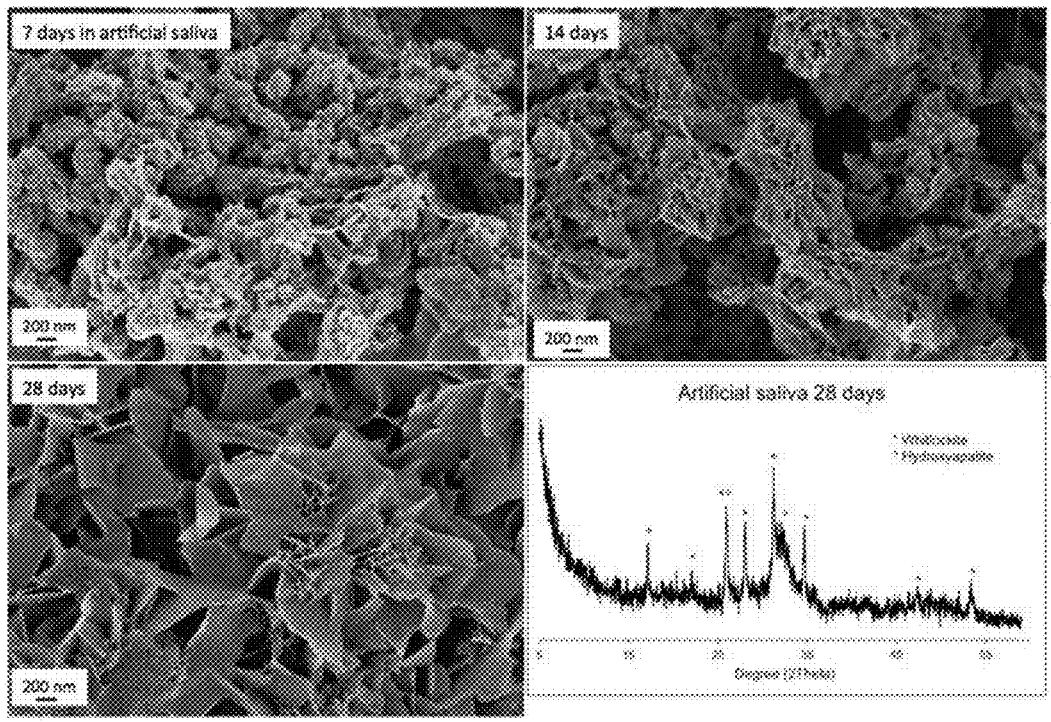
FIG. 15. SEM image and XRD pattern disclosing degradation and crystallization of calcium magnesium phosphate particles according to the present invention in artificial saliva after 7, 14 and 28 days.

The results for tap water are shown in FIG. 14, which demonstrate that the particles retained their characteristic morphology for up to two weeks. After four weeks, the particles had degraded and partly crystallized into hydroxyapatite. In artificial saliva, the particles began to degrade and recrystallize within one week, see FIG. 15. After two weeks there were no spherical particles left, and after four weeks large flake-like crystals had formed. The crystalline phases were identified as hydroxyapatite and whitlockite, which are both naturally occurring minerals in human hard tissue.

Example 24

A composition containing 40 weight % spherical and hollow calcium magnesium phosphate particles, 55 weight % glycerol and 5 weight % free water according to the present invention was stored in a closed contained at room temperature (20-23°) for up to 18 months, after which the characteristics of the composition and particles were evaluated to determine stability.

Figure 16:
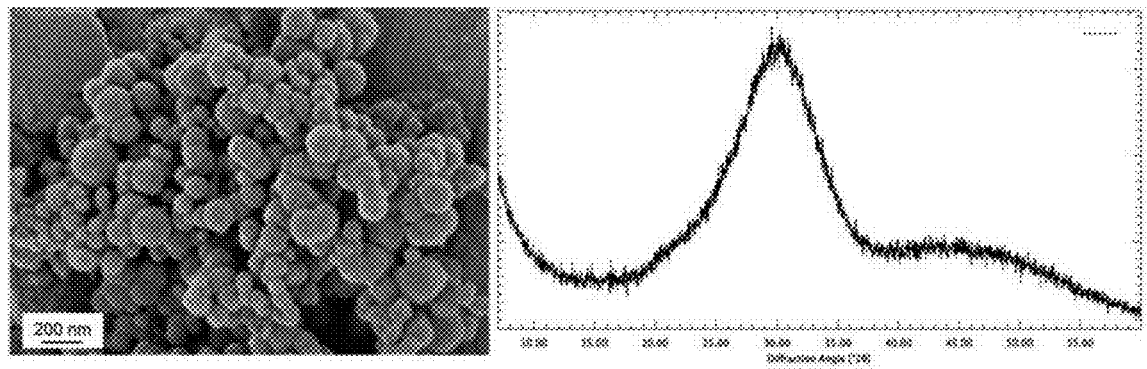
FIG. 16. SEM image and XRD pattern of particles after 18 months storage of composition containing 40 weight % calcium magnesium phosphate particles, 55 weight % glycerol, and 5 weight % free water according to the present invention.

It was found that the characteristics of the composition were maintained, and that the key properties of the particles such as morphology, crystallinity, particle size and chemical composition were preserved. See FIG. 16 for SEM and XRD data. The results indicate that the composition with particles and glycerol according to the present invention is stable, and that the shelf life of the composition is at least 18 months.

Example 25

Chemical reactions and phase transformations such as degradation or crystallization of amorphous calcium phosphate is accelerated at elevated temperatures. To evaluate stability in accelerated conditions, a composition containing 40 weight % spherical and hollow calcium magnesium phosphate particles, 55 weight % glycerol and 5 weight % free water according to the present invention was stored in a closed container at 40° C. for up to 12 months. Characteristics of the composition and particles were then evaluated to determine stability.

Figure 17:
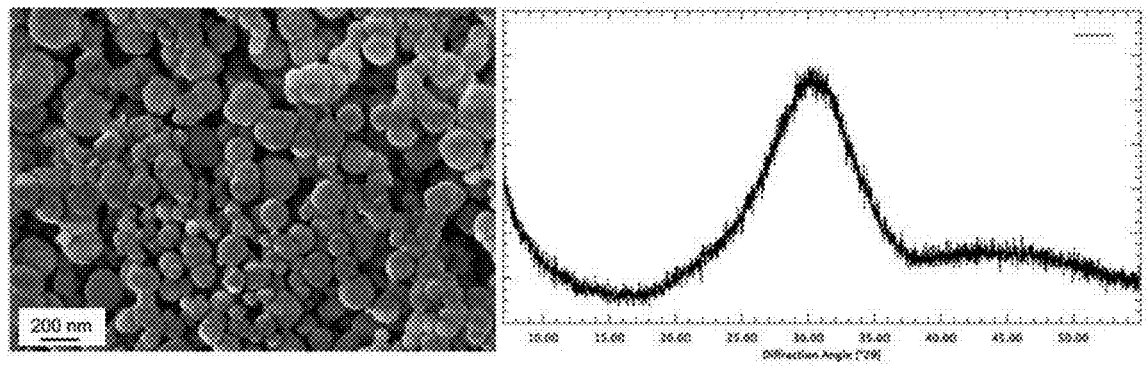
FIG. 17. SEM image and XRD pattern of particles after 12 months accelerated storage of composition containing 40 weight % calcium magnesium phosphate particles, 55 weight % glycerol, and 5 weight % free water according to the present invention.

It was found that the characteristics of the composition were maintained, and that the key properties of the particles such as morphology, crystallinity, particle size and chemical composition were preserved. See FIG. 17 for SEM and XRD data. Applying a conservative acceleration factor of 3 for the storage condition at 40° C., the results indicate that the composition with particles and glycerol according to the present invention is stable and has a projected shelf life of 36 months.

Example 26

Figure 18:
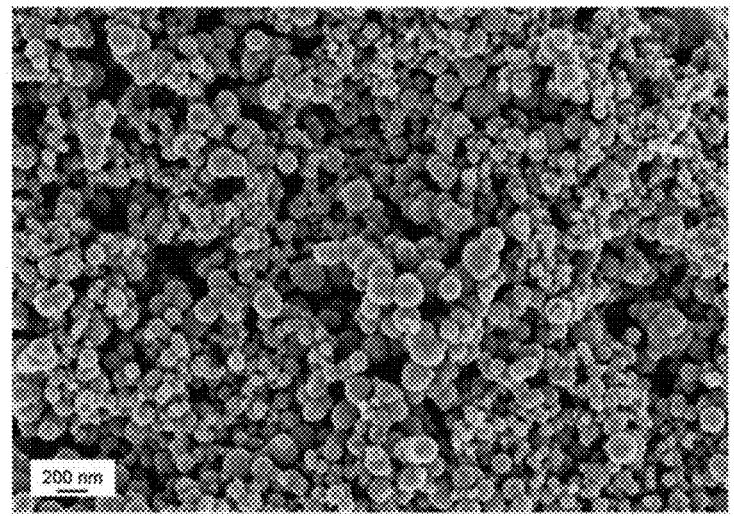
FIG. 18. SEM image of calcium magnesium phosphate particles in desensitizer gel according to the present invention after 18 months ambient storage.

A desensitizing gel containing particles and additives according to the present invention was stored in a product suitable LDPE tube in ambient (20-23° C.) conditions for up to 18 months, during which product properties such as moisture content, consistency and appearance of the particles were evaluated. See FIG. 18 for appearance of the particles in the gel after storage. It was found that evaluated product properties had been maintained, and concluded that product stability of the desensitizing gel is at least 18 months.

Example 27

Figure 19:
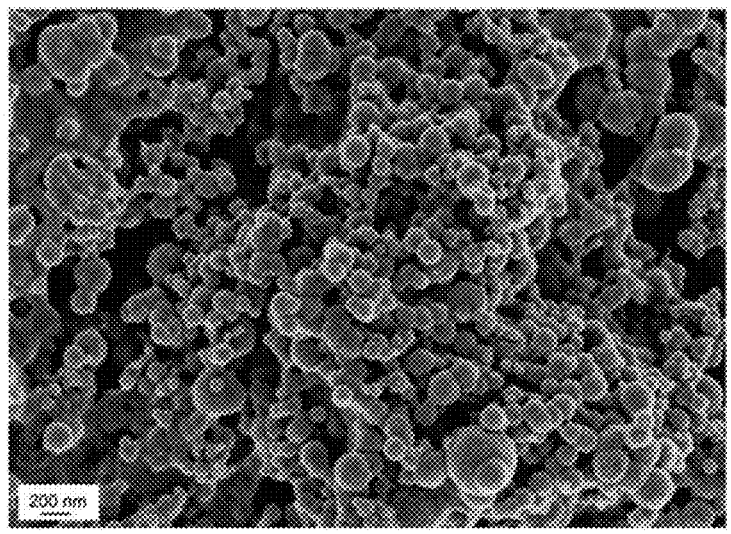
FIG. 19. SEM image of calcium magnesium phosphate particles in desensitizer gel according to the present invention after 12 months accelerated storage.

A desensitizing gel containing particles and additives according to the present invention was stored in a product suitable LDPE tube in accelerated (40° C., >90% rH) conditions for up to 12 months, after which product properties such as moisture content, consistency and appearance of the particles were evaluated. See appearance of the particles after storage in FIG. 19. It was found that tube weight and moisture content of the gel increased due to the high relative humidity storage conditions, but that appearance of the particles and consistency of the gel was essentially maintained. Applying a conservative acceleration factor of 3 for the storage condition results in a tentative shelf life for the desensitizing gel of 36 months.

Example 28

Figure 20:
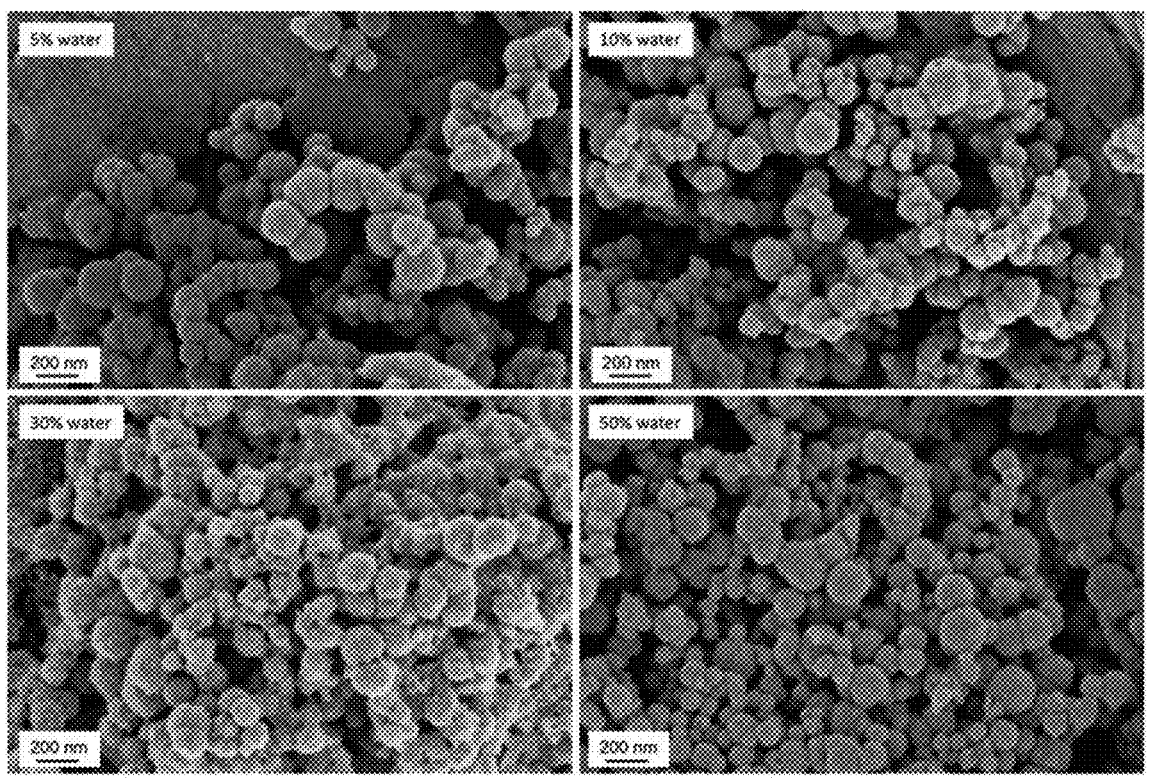
FIG. 20. SEM images of calcium magnesium phosphate particles according to the present invention after storage for 20 weeks in compositions containing 5-50% excess free water.
Figure 21:
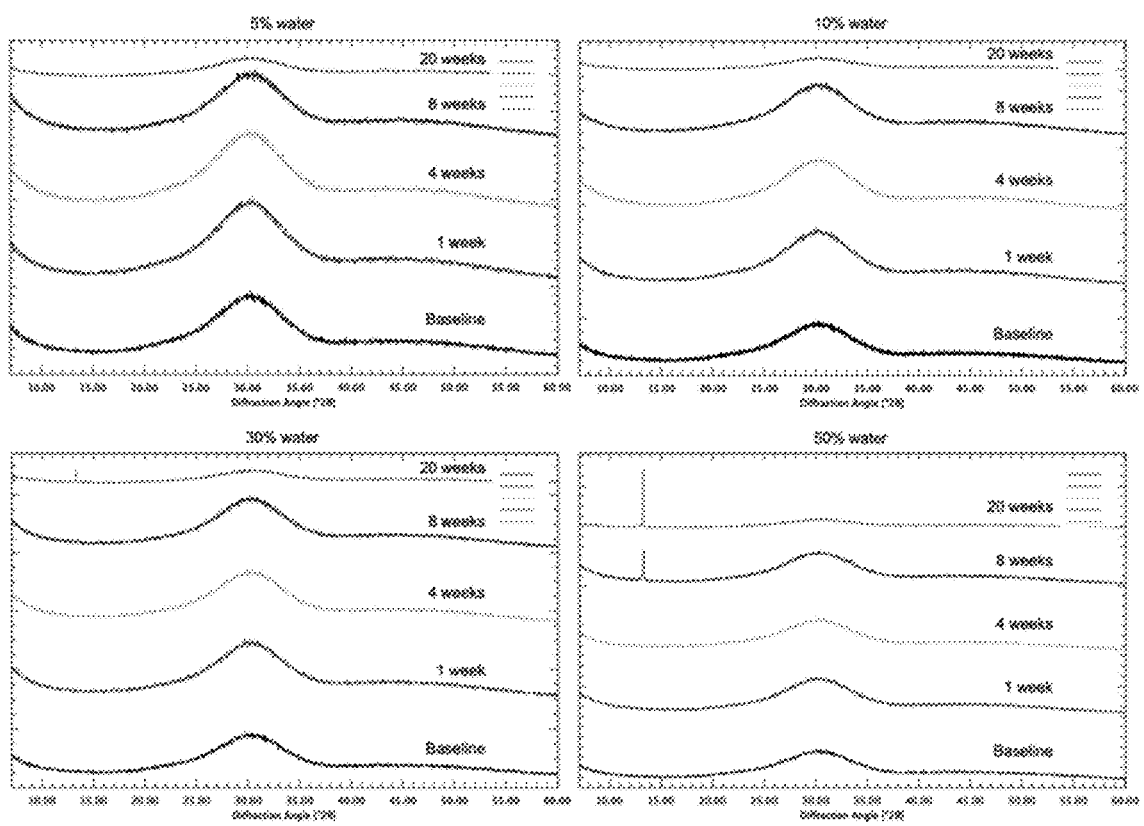
FIG. 21. XRD pattern of calcium magnesium phosphate particles according to the present invention after storage for up to 20 weeks in compositions containing 5-50% excess free water.

To demonstrate the stability of compositions containing particles and glycerol manufactured according to the present invention, even in compositions with excess free water which normally promotes crystallization of ACP, a composition with 40 weight % spherical and hollow calcium magnesium phosphate particles, 55 weight % glycerol and 5 weight % free water according to the present invention was mixed with water to form mixtures containing 5-50 weight % excess free water. These mixtures were stored in ambient (20-23° C.) conditions for up to 20 weeks, then the particles were analyzed by SEM and XRD to record any significant changes in appearance and crystallinity, see results in FIGS. 20 and 21. The outcome demonstrated that the particles remained spherical and amorphous in mixtures with 5 and 10 weight % excess water for the duration of the study (20 weeks). In mixtures with 30 and 50 weight % excess free water there were slight alterations in particle appearance after 20 weeks storage, but a majority of the particles still retained their characteristic spherical shape. An increase in crystallinity was noted for the 50 weight % excess free water sample first after 8 weeks storage.

Example 29

A prototype whitening gel containing 16 weight % carbamide peroxide and 7.5 weight % spherical and hollow calcium magnesium phosphate particles according to the present invention was applied to enamel specimens six hours daily for three days, with intermittent storage in artificial saliva at 37° C. A control whitening gel with 16 weight % carbamide peroxide but without particles was evaluated in parallel on enamel specimens from the same teeth.

Shade evaluation after treatment with the different gels demonstrated that the whitening effect was similar, indicating that the particles according to the present invention did not negatively affect the whitening process. Vickers hardness evaluation (300 gf, 10 s) of the enamel specimens before and after treatment demonstrated that there was a significant increase in hardness for the specimens treated with the particle-containing whitening gel, whereas the hardness change for the specimens treated with the control gel were non-significant based on a two-tailed and paired t-test with a significance level of 0.05, see Table 3. The increase in hardness observed for the specimens treated with the particle-containing whitening gel indicates that the particles induced mineralization of the surface enamel, thereby strengthening the tooth.

TABLE 3

Results of enamel hardness evaluation before and after three days whitening treatment with gels with or without particles according to the present invention.

| Enamel specimen | Treatment | HV before treatment (±SD) | HV after treatment (±SD) | p-value |
|---|---|---|---|---|
| 1A | Particle gel | 313.5 ± 11.6 | 357.5 ± 21.9 | <0.01* |
| 1B | Control gel | 318.2 ± 9.1 | 334.9 ± 17.5 | 0.19 |
| 2A | Particle gel | 294.3 ± 10.4 | 343.6 ± 22.2 | 0.02* |
| 2B | Control gel | 294.8 ± 17.0 | 296.6 ± 12.3 | 0.73 |
| 2C | None | 298.3 ± 23.6 | 298.2 ± 8.5 | 0.99 |

*Significant difference

Example 30

The amorphous calcium phosphate particles according to the present invention are stabilized by magnesium substitution but may still crystallize over time in ambient conditions. The compositions with particles and paste forming compound according to the current invention are formed in part to enable long-term stability of the particles.

Figure 22:
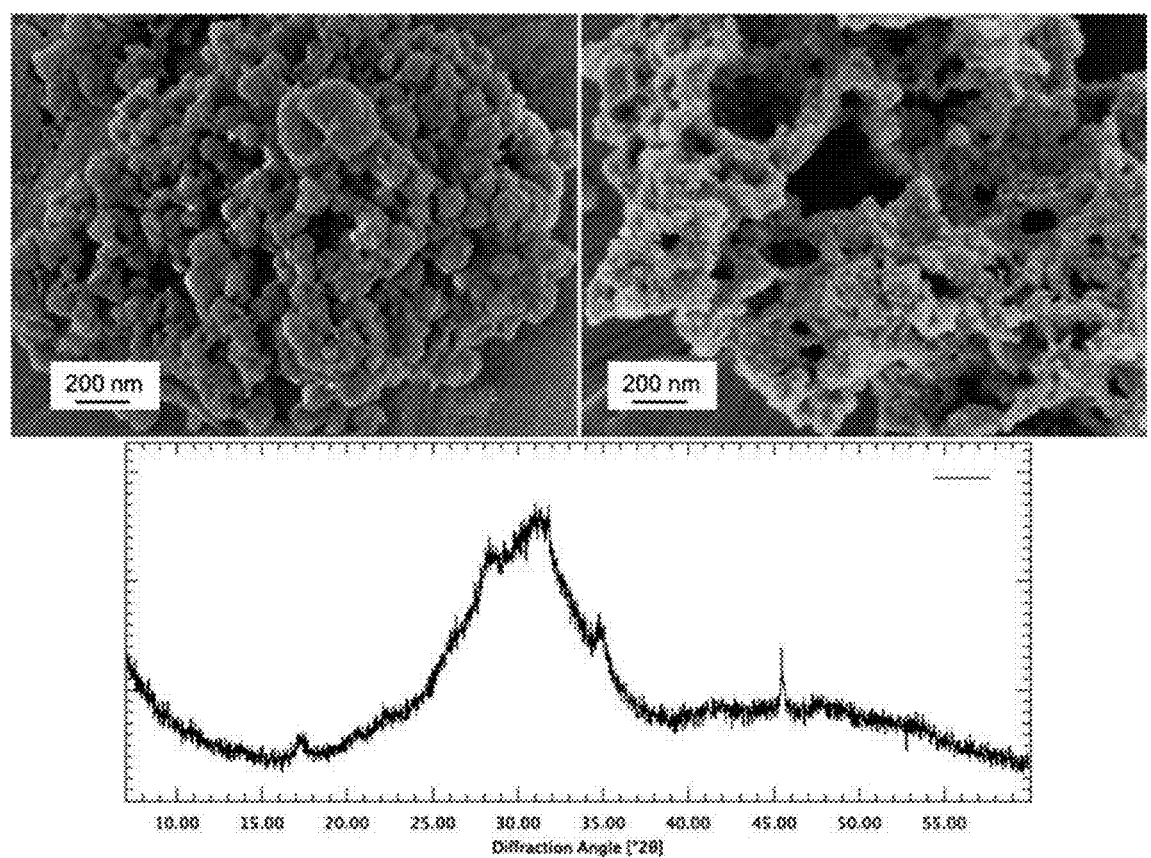
FIG. 22. SEM images and XRD pattern of calcium magnesium phosphate particles according to the present invention after storage as a dry fine powder in a closed container in ambient conditions (20-25° C.) for 11 months.

Particles according to the current invention were stored as a dry fine powder in a closed container under ambient conditions for 11 months to evaluate stability. It was found that some of the particles retained the spherical shape but demonstrated signs of degradation and crystallization. Other particles had transformed completely. XRD evaluation demonstrated an increase in crystallinity, see FIG. 22.

Compared to the particle stability in composition with glycerol (Examples 24 and 25), the degradation/crystallinity of the powder particles was significant.

The invention claimed is:

1. A composition comprising a paste forming compound and X-ray diffraction (XRD) amorphous calcium magnesium phosphate spherical particles having a hollow core and a shell wherein the particles are XRD amorphous and wherein the shell of the particles comprises 15-30 weight % of calcium, 50-70 weight % of phosphate, 5-11 weight % magnesium, and 1 to 20 weight % bound water, and wherein the Ca/P molar ratio is in the range of 0.70 to 1.20, and wherein the (Ca+Mg)/P molar ratio is in the range of 1.00 to 1.70, and wherein the particles have a mean particle size in the range of 100 to 500 nm, and wherein the amount of particles in the composition is 25-50 weight %.

2. The composition according to claim 1 wherein the amount of particles in the composition is 35-45 weight %.

3. The composition according to claim 1 wherein the paste forming compound is selected from glycerol, triglyceride, polyethylene glycol, propylene glycol, polypropylene glycol, polyvinyl alcohol, mineral oil or liquid paraffin.

4. The composition according to claim 1 wherein the spherical particles have a porous shell.

5. The composition according to claim 1 wherein the spherical particles are essentially long range amorphous.

6. The composition according to claim 1 wherein the mean particle size of the spherical particles is 150-450 nm.

7. The composition according to claim 1 wherein the spherical particles comprise 12 to 16 weight % of bound water.

8. The composition according to claim 1 wherein the spherical particles comprises 20-26 weight % of calcium, 52-64 weight % of phosphate, 5-9 weight % of magnesium and 12-16 weight % bound water and wherein the Ca/P ratio is 0.80-1.00 and the (Ca+Mg)/P ratio is 1.15-1.45.

9. The composition according to claim 1 wherein the spherical particles further comprises at least one of the ions selected from sodium, potassium, silicon, zinc, and fluoride.

10. The composition according to claim 1 wherein the spherical particles have an average surface area (BET) of 10-40 m$^2$/g.

11. The compositions according to claim 1 wherein the amount of paste forming compound is at least 50 weight %.

12. The composition according to claim 1 wherein the composition comprises not more than 10 weight % free water.

13. The composition according to claim 1 wherein the composition comprises 25-50 weight % particles, at least 50 weight % paste forming compound, and less than 10 weight % free water.

14. A method of preparing the composition according to claim 1 wherein the method comprises:
 a. providing a first aqueous solution having a pH of 6 to 10 and a first temperature, wherein said first solution comprises dihydrogen phosphate and/or hydrogen phosphate ions and one or more counter ions;
 b. providing a second aqueous solution having a second temperature, wherein said second solution comprises calcium and magnesium ions and one or more counter ions; and wherein the amount of calcium is in molar excess of magnesium;

c. heating the first aqueous solution, the second aqueous solution or both the first and the second aqueous solutions to a first and second elevated temperature respectively;

d. bringing the first and second aqueous solutions into contact with each other giving a third aqueous solution having a third temperature and wherein the amount of phosphate in the third aqueous solution is in molar excess to the total amount of calcium and magnesium;

e. allowing particles to form;

f. collecting the formed particles;

g. optionally washing the isolated particles using a suitable solvent;

h optionally dewatering the washed particles at a fifth temperature until a slurry comprising 70-95 weight % free water is obtained;

i. mixing the spherical particles with a paste forming compound wherein the amount of particles in the composition is 25-50 weight %;

j. dewatering of the mixture of spherical particles and paste forming compound at a seventh temperature; and k. optionally homogenizing the mixture of spherical particles and paste forming compound of to obtain a composition.

15. The method according to claim 14 wherein the paste forming compound is glycerol.

16. The method according to claim 14 wherein the third temperature is 70 to 95° C.

17. The method according to claim 14 wherein difference in temperature between the first temperature and the first elevated temperature and the second temperature and the second elevated temp is at least 40° C.

18. The method according to claim 14 wherein the first and second aqueous solution is brought into contact with each other at a volume ratio of 2:1 to 1:2.

19. The method according to claim 14 wherein the formed and isolated particles are washed at a fourth temperature, preferably at 50-90° C.

20. The method according to claim 14 wherein the formed, isolated and optionally washed particles are partially dewatered preferably using centrifugation or reduced pressure and/or at a fifth temperature, wherein the fifth temperature preferably is 50-150° C.

21. The method according to claim 14 wherein the water in the first and second aqueous solution is tap water or preferably purified water.

22. The method according to claim 14 wherein the solvent in the washing step g is purified water.

23. The method according to claim 14 wherein the pH of the first aqueous solution is 7 to 10.

24. The method according to claim 14 wherein the molar ratio of $H_2PO_4$:$HPO_4$ in the first aqueous solution is in the range of 0-100:75-600.

25. The method according to claim 14 wherein the total concentration of phosphate in the first aqueous solution is 60-800 mM.

26. The method according to claim 14 wherein calcium is in molar excess to magnesium in the second aqueous solution.

27. The method according to claim 14 wherein the amount of phosphate is in molar excess to the total amount of calcium and magnesium ($PO_4$>(Ca+Mg)).

28. The method according to claim 14 wherein the particles are suspended in a slurry before mixing with the paste forming compound wherein the slurry comprises 10-30 weight % particles and 70-90 weight % water.

29. The method according to claim 14 wherein the formed, collected, optionally washed and/or dewatered particles is mixed with a paste forming compound and dried at a seventh temperature in the range of 50-150° C., and are homogenized.

30. A toothpaste, a desensitizing gel, a bleaching paste, a sealant, a dental varnish or a dental prophy paste comprising the composition according to claim 1 wherein the amount of particles is 0.5 to 15 weight %.

31. A bleaching paste comprising the composition according to claim 1 and carbamide peroxide, wherein the amount of particles is 3-10 weight % and the amount of carbamide peroxide is 10-20 weight %.

32. The composition according to claim 1 wherein the mean particle size of the spherical particles is 250-350 nm.

33. The composition according to claim 1 wherein the spherical particles have an average surface area (BET) of 15-35 $m^2$/g.

34. The composition according to claim 1 wherein the spherical particles have an average surface area (BET) of 20-30 $m^2$/g.

35. The compositions according to claim 1 wherein the amount of paste forming compound is at least 55 weight %.

36. The compositions according to claim 1 wherein the amount of paste forming compound is at least 60 weight %.

37. The composition according to claim 1 wherein the composition comprises 5 weight % or less of free water.

38. The composition according to claim 1 wherein the composition comprises 35-45 weight % particles, at least 55 weight % paste forming compound and less than 8 weight % free water.

39. The method according to claim 14 wherein the dewatering of the washed particles at a fifth temperature is done until a slurry comprising 75-85 weight % free water is obtained.

40. The method according to claim 14 wherein the difference in temperature between the first temperature and the first elevated temperature and the second temperature and the second elevated temp is 40-80° C.

41. The method according to claim 14 wherein the first and second aqueous solution is brought into contact with each other at a volume ratio of 1.10:1 to 1:1.10, and brought into contact in a continuous manner.

* * * * *